(12) United States Patent
Shi

(10) Patent No.: US 6,992,063 B2
(45) Date of Patent: Jan. 31, 2006

(54) COMPOSITIONS AND METHOD FOR REGULATING APOPTOSIS

(75) Inventor: Yigong Shi, Plainsboro, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 722 days.

(21) Appl. No.: 09/965,967

(22) Filed: Sep. 28, 2001

(65) Prior Publication Data

US 2002/0177557 A1 Nov. 28, 2002

Related U.S. Application Data

(60) Provisional application No. 60/236,574, filed on Sep. 29, 2000, and provisional application No. 60/256,830, filed on Dec. 20, 2000.

(51) Int. Cl.
*A61K 38/06* (2006.01)

(52) U.S. Cl. ....................................................... 514/16
(58) Field of Classification Search ................. 514/2, 514/16–18; 530/300
See application file for complete search history.

(56) References Cited

U.S. PATENT DOCUMENTS 6,110,691 A    8/2000  Wang et al. .................. 435/7.1

OTHER PUBLICATIONS

Srinivasa M. Srinivasula, et al; *Molecular Determinants of the Caspase–Promoting Activity of Smac/DIABLO and its role in the Death of Receptor Pathway*; J. Biol. Chem.; vol. 275, No. 46, Issue of Nov. 17, 2000; pp. 36152–36157.
Ambrosini, G., et al., "Induction of apoptosis and inhibition of cell proliferation by survivin gene targeting," *J. Biol. Chem.*, 1998, 273(18), 11177–11182.
Ashhab, Y., et al., "Two splicing variants of a new inhibitor of apoptosis gene with different biological properties and tissue distribution pattern," *FEBS Lett.*, 2001, 495, 56–60.
Brunger, A.T., X–PLOR, a System for Crystallography and NMR, *Yale University Press*, New Haven, CT., 1991.
Chai, et al., "Structural and biochemical basis of apoptotic activation by Smac/DIABLO," *Nature*, 2000, 406, 855–862.
Chen, P., et al., "Grim, a novel cell death gene in drosophila," *Genes & Devel.*, 1996, 10, 1773–1782.
Deveraux, Q.L., et al., "IAP family proteins—suppressors of apoptosis," *Genes & Dev.*, 1999, 13, 239–252.
Du, C., et al., "Smac, a motochondrial protein that promotes cytochrome c–dependent caspase activation by eliminating IAP inhibition," *Cell*, 2000, 102, 33–42.
Goyal, L., et al., "Induction of apoptosis by drosophila reaper, hid and grim through inhibition of IAP function," *EMBO J.*, 2000, 19(4), 589–597.

Hay, B., "Understanding IAP function and regulation: a view from drosophila," *Cell Death Differ.*, 2000, 7, 1045–1056.
Hruby, V.J., et al., "Conformational and topographical considerations in designing agonist peptidomimetics from peptide leads," *Curr. Med. Chem.*, 2000, 7, 945–970.
Hruby, V.J., et al., "Synthesis of oligopeptide and peptidomimetic libraries," *Curr. Op. In Chem. Biol.*, 1997, 1, 114–119.
Jones, T.A., et al., "Improved methods for building protein models in electron density maps and the location of errors in these models," *Acta Crystallogr.*, 1991, A47, 110–119.
Kasof, G.M., et al., "Livin, a novel inhibitor of apoptosis protein family member," *J. Biol. Chem.*, 2001, 276(5), 3238–3246.
Kraulis, P.J., "*Molscript*: a program to produce both detailed and schematic plots of protein structures," *J. Appl. Crystallogr.*, 1991, 24, 946–950.
Lisi, S., et al., "Diverse domains of THREAD/DIAP1 are required to inhibit apoptosis induced by REAPER and HID in drosophila," *Genetics*, 2000, 154, 669–678.
Liu, Z., "Structural basis for binding of Smac/DIABLO to the XIAP BIR3 domain," *Nature*, Dec. 2000, 1004–1008.
McCarthy, J.V., et al., "Apoptosis induced by *drosophila* reaper and grim in a human syustem," *J. Biol. Chem.*, 1998, 273(37), 24009–24015.
Morgan, B.A., et al., "Chapter 26. Approaches to the discovery of non–peptide ligands for peptide receptors and peptidases," *Ann. Rep. Med. Chem.*, 1989, 243–252.
Navaza, J., "*AmoRe*: an automated package for molecular replacement," *Acta Crystallogr*, 1994, A50, 157–163.
Nicholls, A., et al., "Protein folding and association: insights from the interfacial and thermodynamic properties of hydrocarbons," *Proteins: Struct. Funct. & Genet.*, 1991, 11, 281–296.
Ripka, A.S., et al., "Peptidomimetic design," *Curr. Op. Chem. Biol.*, 1998, 2, 441–452.
Srinivasula, S.M., et al., "A conserved XIAP–interaction motif in caspase–9 and Smac/DIABLO regulates caspase activity and apoptosis," *Nature*, 2001, 410, 112–116.

(Continued)

*Primary Examiner*—Jon Weber
*Assistant Examiner*—Sheridan Snedden
(74) *Attorney, Agent, or Firm*—Raymond A. Miller; Pepper Hamilton LLP

(57) ABSTRACT

Peptides and peptidomimetics capable of modulating apoptosis through their interaction with cellular IAPs (inhibitor of apoptosis proteins) are disclosed. The peptides and mimetics are based on the N-terminal tetrapeptide of IAP-binding proteins, such as Smac/DIABLO, Hid, Grim and Reaper, which interact with a specific surface groove of IAP. Also disclosed are methods of using these peptides and peptidomimetics for therapeutic purposes and for rational drug design.

14 Claims, 14 Drawing Sheets

(10 of 14 Drawing Sheet(s) Filed in Color)

OTHER PUBLICATIONS

Sun, C., et al., "NMR structure and mutagenesis of the third bir domain of the inhibitor of apoptosis protein XIAP," *J. Biol. Chem.*, 2000, 275(43), 33777–33781.

Terwilliger, T.C., et al., "The CCP4 suite: Programs for protein crystallography," *Acta Crystallogr.*, 1994, D50, 760–763.

Terwilliger, T.C., et al., "Correlated phasing of multiple isomorphous replacement data," *Acta Crystallogr.*, 1996, D52, 749–757.

Verhagen, A.M., et al., "Identification of DIABLO, a mammalian protein that promotes apoptosis by binding to and antagonizing IAP proteins," *Cell*, 2000, 102, 43–53.

Vucic, D., et al., "Inhibition of reaper–induced apoptosis by interaction with inhibitor of apoptosis proteins (IAPs)," *Proc. Natl. Acad. Sci. USA*, 1997, 94, 10183–10188.

Vucic, D., et al., "ML–IAP, a novel inhibitor of apoptosis that is preferentially expressed in human melanomas," *Curr. Biol.*, 2000, 10, 1359–1366.

| | | | | | | | |
|---|---|---|---|---|---|---|---|
| Smac/DIABLO | A | V | P | I | A | Q | K |
| Reaper | A | V | A | F | Y | I | P |
| Grim | A | I | A | Y | F | L | P |
| Hid | A | V | P | F | Y | L | P |
| hCasp-9 | A | T | P | F | Q | E | G |
| mCasp-9 | A | V | P | Y | Q | E | G |
| xCasp-9 | A | T | P | V | F | S | G |

SEQUENCE LISTING

```
<160> NUMBER OF SEQ ID NOS: 30

<210> SEQ ID NO 1
<211> LENGTH: 4
<212> TYPE: PRT
<213> ORGANISM: Homo sapiens

<400> SEQUENCE: 1

Ala Val Pro Ile
1

<210> SEQ ID NO 2
<211> LENGTH: 4
<212> TYPE: PRT
<213> ORGANISM: Drosophila melanogaster

<400> SEQUENCE: 2

Ala Val Ala Phe
1

<210> SEQ ID NO 3
<211> LENGTH: 4
<212> TYPE: PRT
<213> ORGANISM: Drosophila melanogaster

<400> SEQUENCE: 3

Ala Ile Ala Tyr
1

<210> SEQ ID NO 4
<211> LENGTH: 4
<212> TYPE: PRT
<213> ORGANISM: Drosophila melanogaster

<400> SEQUENCE: 4

Ala Val Pro Phe
1

<210> SEQ ID NO 5
<211> LENGTH: 4
<212> TYPE: PRT
<213> ORGANISM: Homo sapiens

<400> SEQUENCE: 5

Ala Thr Pro Phe
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

Ala Val Pro Tyr
1

<210> SEQ ID NO 7
```

```
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Ala Thr Pro Val
1

<210> SEQ ID NO 8
<211> LENGTH: 7
<212> TYPE: PRT
<213> ORGANISM: Homo sapiens

<400> SEQUENCE: 8

Ala Val Pro Ile Ala Gln Lys
1               5

<210> SEQ ID NO 9
<211> LENGTH: 7
<212> TYPE: PRT
<213> ORGANISM: Drosophila melanogaster

<400> SEQUENCE: 9

Ala Val Ala Phe Tyr Ile Pro
1               5

<210> SEQ ID NO 10
<211> LENGTH: 7
<212> TYPE: PRT
<213> ORGANISM: Drosophila melanogaster

<400> SEQUENCE: 10

Ala Ile Ala Tyr Phe Leu Pro
1               5

<210> SEQ ID NO 11
<211> LENGTH: 7
<212> TYPE: PRT
<213> ORGANISM: Drosophila melanogaster

<400> SEQUENCE: 11

Ala Val Pro Phe Tyr Leu Pro
1               5

<210> SEQ ID NO 12
<211> LENGTH: 7
<212> TYPE: PRT
<213> ORGANISM: Homo sapiens

<400> SEQUENCE: 12

Ala Thr Pro Phe Gln Glu Gly
1               5

<210> SEQ ID NO 13
<211> LENGTH: 7
<212> TYPE: PRT
<213> ORGANISM: Mus musculus

<400> SEQUENCE: 13

Ala Val Pro Tyr Gln Glu Gly
1               5

<210> SEQ ID NO 14
```

-continued

```
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Ala Thr Pro Val Phe Ser Gly
1               5

<210> SEQ ID NO 15
<211> LENGTH: 10
<212> TYPE: PRT
<213> ORGANISM: Drosophila melanogaster

<400> SEQUENCE: 15

Ala Val Pro Phe Tyr Leu Pro Glu Gly Gly
1               5                   10

<210> SEQ ID NO 16
<211> LENGTH: 10
<212> TYPE: PRT
<213> ORGANISM: Drosophila melanogaster

<400> SEQUENCE: 16

Ala Ile Ala Tyr Phe Ile Pro Asp Gln Ala
1               5                   10

<210> SEQ ID NO 17
<211> LENGTH: 10
<212> TYPE: PRT
<213> ORGANISM: Drosophila melanogaster

<400> SEQUENCE: 17

Ala Val Ala Phe Tyr Ile Pro Asp Gln Ala
1               5                   10

<210> SEQ ID NO 18
<211> LENGTH: 10
<212> TYPE: PRT
<213> ORGANISM: Homo sapiens

<400> SEQUENCE: 18

Ala Val Pro Ile Ala Gln Lys Ser Glu Pro
1               5                   10

<210> SEQ ID NO 19
<211> LENGTH: 109
<212> TYPE: PRT
<213> ORGANISM: Drosophila melanogaster

<400> SEQUENCE: 19

Lys Asn Asn Ile Asn Lys Thr Arg Met Asn Asp Leu Asn Arg Glu Glu
1               5                   10                  15

Thr Arg Leu Lys Thr Phe Thr Asp Trp Pro Leu Asp Trp Leu Asp Lys
                20                  25                  30

Arg Gln Leu Ala Gln Thr Gly Met Tyr Phe Thr His Ala Gly Asp Lys
            35                  40                  45

Val Lys Cys Phe Phe Cys Gly Val Glu Ile Gly Cys Trp Glu Gln Glu
        50                  55                  60

Asp Gln Pro Val Pro Glu His Gln Arg Trp Ser Pro Asn Cys Pro Leu
65                  70                  75                  80

Leu Arg Arg Arg Thr Thr Asn Asn Val Pro Ile Asn Ala Glu Ala Leu
```

```
                    85                  90                  95
Asp Arg Ile Leu Pro Pro Ile Ser Tyr Asp Ile Cys Gly
                100                 105

<210> SEQ ID NO 20
<211> LENGTH: 107
<212> TYPE: PRT
<213> ORGANISM: Homo sapiens

<400> SEQUENCE: 20

Pro Asn Ser Thr Asn Leu Pro Arg Asn Pro Ser Met Ala Asp Tyr Glu
1               5                   10                  15

Ala Arg Ile Phe Thr Phe Gly Thr Trp Ile Tyr Ser Val Asn Lys Glu
            20                  25                  30

Gln Leu Ala Arg Ala Gly Phe Tyr Ala Leu Gly Glu Gly Asp Lys Val
        35                  40                  45

Lys Cys Phe His Cys Gly Gly Gly Leu Thr Asp Trp Lys Pro Ser Glu
50                  55                  60

Asp Pro Trp Glu Gln His Ala Lys Trp Tyr Pro Gly Cys Lys Tyr Leu
65                  70                  75                  80

Leu Glu Gln Lys Gly Gln Glu Tyr Ile Asn Asn Ile His Leu Thr His
                85                  90                  95

Ser Leu Glu Glu Cys Leu Val Arg Thr Thr Glu
            100                 105

<210> SEQ ID NO 21
<211> LENGTH: 110
<212> TYPE: PRT
<213> ORGANISM: Homo sapiens

<400> SEQUENCE: 21

Ile Ser Asp Thr Ile Tyr Pro Arg Asn Pro Ala Met Tyr Cys Glu Glu
1               5                   10                  15

Ala Arg Leu Lys Ser Phe Gln Asn Trp Pro Asp Tyr Ala His Leu Thr
            20                  25                  30

Pro Arg Glu Leu Ala Ser Ala Gly Leu Tyr Tyr Thr Gly Ile Gly Asp
        35                  40                  45

Gln Val Gln Cys Phe Cys Cys Gly Gly Lys Leu Lys Asn Trp Glu Pro
50                  55                  60

Cys Asp Arg Ala Trp Ser Glu His Arg Arg His Phe Pro Asn Cys Phe
65                  70                  75                  80

Phe Val Leu Gly Arg Asn Leu Asn Ile Arg Ser Glu Ser Asp Ala Val
                85                  90                  95

Ser Ser Asp Arg Asn Phe Pro Asn Ser Thr Asn Leu Pro Arg
            100                 105                 110

<210> SEQ ID NO 22
<211> LENGTH: 110
<212> TYPE: PRT
<213> ORGANISM: Homo sapiens

<400> SEQUENCE: 22

Thr Cys Val Pro Ala Asp Ile Asn Lys Glu Glu Glu Phe Val Glu Glu
1               5                   10                  15

Phe Asn Arg Leu Lys Thr Phe Ala Asn Phe Pro Ser Gly Ser Pro Val
            20                  25                  30

Ser Ala Ser Thr Leu Ala Arg Ala Gly Phe Leu Tyr Thr Gly Glu Gly
        35                  40                  45
```

```
Asp Thr Val Arg Cys Phe Ser Cys His Ala Val Asp Arg Trp Gln
         50                  55                  60

Tyr Gly Asp Ser Ala Val Gly Arg His Arg Lys Val Ser Pro Asn Cys
 65                  70                  75                  80

Arg Phe Ile Asn Gly Phe Tyr Leu Glu Asn Ser Ala Thr Gln Ser Thr
                 85                  90                  95

Asn Ser Gly Ile Gln Asn Gly Gln Tyr Lys Val Glu Asn Tyr
            100                 105                 110

<210> SEQ ID NO 23
<211> LENGTH: 98
<212> TYPE: PRT
<213> ORGANISM: Homo sapiens

<400> SEQUENCE: 23

Met Gly Ala Pro Thr Leu Pro Pro Ala Trp Gln Pro Phe Leu Lys Asp
 1               5                  10                  15

His Arg Ile Ser Thr Phe Lys Asn Trp Pro Phe Leu Glu Gly Cys Ala
                 20                  25                  30

Cys Thr Pro Glu Arg Met Ala Glu Ala Gly Phe Ile His Cys Pro Thr
             35                  40                  45

Glu Asn Glu Pro Asp Leu Ala Gln Cys Phe Phe Cys Phe Lys Glu Leu
         50                  55                  60

Glu Gly Trp Glu Pro Asp Asp Asp Pro Ile Glu Glu His Lys Lys His
 65                  70                  75                  80

Ser Ser Gly Cys Ala Phe Leu Ser Val Lys Lys Gln Phe Glu Glu Leu
                 85                  90                  95

Thr Leu

<210> SEQ ID NO 24
<211> LENGTH: 4
<212> TYPE: PRT
<213> ORGANISM: Homo sapiens

<400> SEQUENCE: 24

Met Val Pro Ile
 1

<210> SEQ ID NO 25
<211> LENGTH: 13
<212> TYPE: PRT
<213> ORGANISM: Drosophila melanogaster

<400> SEQUENCE: 25

Met Thr Ser Ala Val Pro Ile Ala Gln Lys Ser Glu Pro
 1               5                  10

<210> SEQ ID NO 26
<211> LENGTH: 11
<212> TYPE: PRT
<213> ORGANISM: Drosophila melanogaster

<400> SEQUENCE: 26

Met Ala Val Pro Phe Tyr Leu Pro Glu Gly Gly
 1               5                  10

<210> SEQ ID NO 27
<211> LENGTH: 11
<212> TYPE: PRT
<213> ORGANISM: Drosophila melanogaster
```

```
<400> SEQUENCE: 27

Met Ala Val Ala Phe Tyr Ile Pro Asp Gln Ala
1               5                   10

<210> SEQ ID NO 28
<211> LENGTH: 11
<212> TYPE: PRT
<213> ORGANISM: Drosophila melanogaster

<400> SEQUENCE: 28

Met Ala Ile Ala Tyr Phe Ile Pro Asp Gln Ala
1               5                   10

<210> SEQ ID NO 29
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: X is V, T, or I
<220> FEATURE:
<221> NAME/KEY: misc_feature
<222> LOCATION: (3)..(3)
<223> OTHER INFORMATION: X is P or A
<220> FEATURE:
<221> NAME/KEY: misc_feature
<222> LOCATION: (4)..(4)
<223> OTHER INFORMATION: X is F, Y, I, or V

<400> SEQUENCE: 29

Ala Xaa Xaa Xaa
1

<210> SEQ ID NO 30
<211> LENGTH: 109
<212> TYPE: PRT
<213> ORGANISM: Drosophila melanogaster

<400> SEQUENCE: 30

Ala Ser Gly Asn Tyr Phe Pro Gln Tyr Pro Glu Tyr Ala Ile Glu Thr
1               5                   10                  15

Ala Arg Leu Arg Thr Phe Glu Ala Trp Pro Arg Asn Leu Lys Gln Lys
            20                  25                  30

Pro His Gln Leu Ala Glu Ala Gly Phe Phe Tyr Thr Gly Val Gly Asp
        35                  40                  45

Arg Val Arg Cys Phe Ser Cys Gly Gly Gly Leu Met Asp Trp Asn Asp
    50                  55                  60

Asn Asp Glu Pro Trp Glu Gln His Ala Leu Trp Leu Ser Gln Cys Arg
65                  70                  75                  80

Phe Val Lys Leu Met Lys Gly Gln Leu Tyr Ile Asp Thr Val Ala Ala
                85                  90                  95

Lys Pro Val Leu Ala Glu Glu Lys Glu Glu Ser Thr Ser
            100                 105
```

COMPOSITIONS AND METHOD FOR REGULATING APOPTOSIS

This application claims priority under 35 U.S.C. §119(e)(1) to U.S. Provisional Application No. 60/236,474, filed Sept. 29, 2000, and to U.S. Provisional Application No. 60/256,830, filed Dec. 20, 2000, the entireties of both of which are incorporated by reference herein.

Pursuant to 35 U.S.C. §202(c), it is acknowledged that the U.S. Government has certain rights in the invention described herein, which was made in part with funds from the National Institutes of Health, Grant No. CA90269.

FIELD OF THE INVENTION

The present invention relates to cell biology and control of cell proliferation. In particular, the invention provides peptides and peptidomimetics capable of modulating apoptosis through their interaction with cellular IAPs (inhibitor of apoptosis proteins). The invention further provides methods of using these peptides and peptidomimetics for therapeutic purposes and for rational drug design.

BACKGROUND OF THE INVENTION

Various scientific articles, patents and other publications are referred to throughout the specification. Each of these publications is incorporated by reference herein in its entirety.

Apoptosis (programmed cell death) plays a central role in the development and homeostasis of all multi-cellular organisms. Alterations in apoptotic pathways have been implicated in many types of human pathologies, including developmental disorders, cancer, autoimmune diseases, as well as neuro-degenerative disorders.

Thus, the programmed cell death pathways have become attractive targets for development of therapeutic agents. In particular, since it is conceptually easier to kill than to sustain cells, attention has been focused on anti-cancer therapies using pro-apoptotic agents such as conventional radiation and chemo-therapy. These treatments are generally believed to trigger activation of the mitochondria-mediated apoptotic pathways. However, these therapies lack molecular specificity, and more specific molecular targets are needed.

Apoptosis is executed primarily by activated caspases, a family of cysteine proteases with aspartate specificity in their substrates. Caspases are produced in cells as catalytically inactive zymogens and must be proteolytically processed to become active proteases during apoptosis. In normal surviving cells that have not received an apoptotic stimulus, most caspases remain inactive. Even if some caspases are aberrantly activated, their proteolytic activity can be fully inhibited by a family of evolutionarily conserved proteins called IAPs (inhibitors of apoptosis proteins) (Deveraux & Reed, *Genes Dev.* 13, 239–252, 1999). Each of the IAPs contains 1–3 copies of the so-called BIR (baculoviral IAP repeat) domains and directly interacts with and inhibits the enzymatic activity of mature caspases. Several distinct mammalian IAPs including XIAP, survivin, and Livin/ML-IAP (Kasof & Gomes, *J. Biol. Chem.* 276, 3238–3246, 2001; Vucic et al. *Curr. Biol.* 10, 1359–1366, 2000; Ashhab et al. *FEBS Lett.* 495, 56–60, 2001), have been identified, and they all exhibit anti-apoptotic activity in cell culture (Deveraux & Reed, 1999, supra). As IAPs are expressed in most cancer cells, they may directly contribute to tumor progression and subsequent resistance to drug treatment.

In normal cells signaled to undergo apoptosis, however, the IAP-mediated inhibitory effect must be removed, a process at least in part performed by a mitochondrial protein named Smac (second mitochondria-derived activator of caspases; Du et al. *Cell* 102, 33–42, 2000) or DIABLO (direct IAP binding protein with low pI; Verhagen et al. *Cell* 102, 43–53, 2000). Smac, synthesized in the cytoplasm, is targeted to the inter-membrane space of mitochondria. Upon apoptotic stimuli, Smac is released from mitochondria back into the cytosol, together with cytochrome c. Whereas cytochrome c induces multimerization of Apaf-1 to activate procaspase-9 and -3, Smac eliminates the inhibitory effect of multiple IAPs. Smac interacts with all IAPs that have been examined to date, including XIAP, c-IAP1, c-IAP2, and survivin (Du et al., 2000, supra; Verhagen et al., 2000, supra). Thus, Smac appears to be a master regulator of apoptosis in mammals.

Smac is synthesized as a precursor molecule of 239 amino acids; the N-terminal 55 residues serve as the mitochondria targeting sequence that is removed after import (Du et al., 2000, supra). The mature form of Smac contains 184 amino acids and behaves as an oligomer in solution (Du et al., 2000, supra). Smac and various fragments thereof have been proposed for use as targets for identification of therapeutic agents. U.S. Pat. No. 6,110,691 to Wang et al. describes the Smac polypeptide and fragments ranging from at least 8 amino acid residues in length. However, the patent neither discloses nor teaches a structural basis for choosing a particular peptide fragment of Smac for use as a therapeutic agent or target. Indeed, despite its importance in cell death, no precise structural information on Smac and its precise binding target on XIAP has been available heretofore, and rational design of a drug having the binding functionality of Smac therefore has not been possible.

Similar to mammals, flies contain two IAPs, DIAP1 and DIAP2, that bind and inactivate several *Drosophila* caspases (Hay, *Cell Death Differ.* 7, 1045–1056, 2000). DIAP1 contains two BIR domains; the second BIR domain (BIR2) is necessary and sufficient to block cell death in many contexts. In *Drosophila* cells, the anti-death function of DIAP1 is removed by three pro-apoptotic proteins, Hid, Grim, and Reaper, which physically interact with the BIR2 domain of DIAP1 and remove its inhibitory effect on caspases. Thus Hid, Grim, and Reaper represent the functional homologs of the mammalian protein Smac. However, except for their N-terminal 10 residues, Hid, Grim, and Reaper share no sequence homology with one another. Moreover, there is no apparent homology between the three *Drosophila* proteins and Smac. Further, as for Smac, there is currently no structural information available for any of these *Drosophila* proteins that could offer an explanation as to how proteins with such divergent sequences could act as functional homologs.

The present lack of structural information for the aforementioned IAP binding proteins prevents their use as targets for drug screening and rational drug design. Thus, a need exists to identify structural features of these proteins that underlie their ability to facilitate cellular apoptosis through binding to IAPs.

SUMMARY OF THE INVENTION

The present invention features peptides, peptidomimetics and methods of their use for promoting or otherwise regulating apotosis in cells, through a pathway involving the Inhibitor of Apoptosis Proteins (IAPs), exemplified by XIAP and DIAP, and the mitochondrial IAP-binding proteins Smac, Hid, Grim, Reaper and others. The cellular function of IAPs is to suppress programmed cell death, whereas Smac and other IAP binding proteins (IAP-BPs) relieve that suppression. The inventor has discovered that the activity of the mammalian IAP-BP Smac is dependent upon binding of its N-terminal four residues to a featured surface groove in a portion of XIAP referred to as the BIR3 domain. This binding prevents XIAP from exerting its apoptosis-suppressing function in the cell. The inventor has now further demonstrated that a synthetic peptide comprising or mimicking the structural and biological features of the Smac amino-terminal tetrapeptide is itself capable of relieving XIAP-mediated suppression of apoptosis in mammalian cells. Accordingly, this novel peptide, and molecules that mimic the structure and function of this peptide, may be used as therapeutic agents to promote apoptosis in cells.

Further, the inventor has now determined the crystal structure of the BIR2 domain of the *Drosophila* IAP (DIAP1) in complex with N-terminal peptides of the *Drosophila* pro-apoptotic proteins Hid, Grim and Veto. The structures of these complexes are very similar to that of the XIAP-BIR3 complexed with the Smac peptide.

Thus, according to one aspect of the invention, a synthetic tetrapeptide is provided, which binds an IAP and relieves IAP-mediated inhibition of caspase activity, wherein the tetrapeptide binds a surface groove within a BIR domain of the IAP. The synthetic tetrapeptide preferably binds a BIR2 or BIR3 domain and comprises an amino acid sequence the same as an N-terminal sequence of a cellular IAP-binding protein.

In preferred embodiments, the tetrapeptide comprises the sequence X1-X2-X3-X4 (SEQ ID NO:29), wherein X1 is A, X2 is V, T or I, X3 is P or A, and X4 is F, Y, I or V. In other embodiments, the tetrapeptide is supplemented with one or more of up to three additional amino acid residues comprising a sequence the same as a sequence of a cellular IAP-binding protein in residues 5–7 of its N-terminus. In preferred embodiments, the fifth position is Y or F, the sixth position is L or I, and the seventh position is P.

The present invention also features a non-peptide or partial peptide mimetic of any of the aforementioned synthetic peptides.

In another aspect, the invention provides a method of stimulating apoptosis in a cell, comprising administering to the cell aforementioned synthetic tetrapeptide, in an amount sufficient to stimulate the apoptosis in the cell. In one embodiment, the cell is a cultured cell. In another embodiment, the cell is disposed within a living organism. Mammals are the preferred organism, and humans are most preferred.

According to another aspect of the invention, a compound that binds an Inhibitor of Apoptosis Protein (IAP) and relieves IAP-mediated inhibition of caspase activity is provided. The compound has a formula $R_1-R_2-R_3-R_4$, wherein $R_1$ is A or a mimetic of A; $R_2$ is V, T or I, or a mimetic of V, T or I; $R_3$ is P or A, or a mimetic of P or A; and $R_4$ is F, Y, I or V, or a mimetic of F, Y, I or V. In alternative embodiments, the compound may comprise the formula $R_1-R_2-R_3-R4-R_5-R_6-R_7$, wherein $R_1$ is A or a mimetic of A; $R_2$ is V, T or I, or a mimetic of V, T or I; $R_3$ is P or A, or a mimetic of P or A; and $R_4$ is F, Y, I or V, or a mimetic of F, Y, I or V; $R_5$ is missing, or is Y or F, or a mimetic of Y or F; $R_6$ is present only if $R_5$ is present, and is L or I, or a mimetic of L or I; and $R_7$ is present only if $R_5$ and $R_6$ are present, and is P or a mimetic of P.

The present invention also features a method and assay for rational drug design of agents that can, like the Smac tetrapeptide, bind to the BIR3 domain of XIAP, thereby relieving XIAP-mediated suppression of apoptosis. A similar rational drug design can be based on the analogous interaction of the *Drosophila* Veto, Hid and Grim proteins with the BIR2 domain of DIAP1.

Thus, according to another aspect of the invention, a method is provided for making a drug suitable for treating cell proliferative disease in a mammal by promoting apoptosis in proliferatively diseased cells. The method comprises: (a) constructing a compound that binds a mammalian IAP and relieves IAP-mediated inhibition of caspase activity, wherein the compound binds a surface groove within a BIR3 domain of the IAP; and (b) determining whether the compound promotes apoptosis in a proliferatively diseased cell, an affirmative determination indicating that the drug is suitable for treating the cell proliferative disease.

The invention also provides a method of screening for a compound that binds an IAP at a surface groove within a BIR domain. The method comprises: (a) providing a synthetic tetrapeptide of the invention and a selected IAP to which it binds; (b) combining the tetrapeptide and the IAP in the presence of a test compound under conditions wherein, in the absence of the test compound, a pre-determined quantity of the tetrapeptide would bind the LAP; and (c) determining if the quantity of the tetrapeptide bound to the IAP is decreased in the presence of the test compound, the decrease being indicative that the test compound binds the IAP and relieves IAP-mediated inhibition of caspase activity. This method may comprise additional assay steps, such as determining if the test compound modulates IAP-mediated inhibition of caspase activity and determining if the test compound modulates cellular apoptosis.

Other features and advantages of the invention will be understood by reference to the drawings, detailed description and examples that follow.

BRIEF DESCRIPTION OF THE DRAWINGS

The file of this patent contains at least one drawing/photograph executed in color. Copies of this patent with color drawing(s)/photograph(s) will be provided by the Office upon request and payment of the necessary fee.

FIG. 1. Sequence alignment representation of an evolutionarily conserved family of IAP-binding motifs. The tetrapeptide motif has the consensus sequence A-(V/T/I)-(P/A)-(F/Y/I/V) (SEQ ID NO:29), where the invariable Ala is indicated by an arrow. The *Drosophila* proteins Reaper/Grim/Hid have an additional binding component (Example 3) (conserved residues 6–7, shaded in light gray). The sequences are: Smac/DIABLO, AVPIAQK (SEQ ID NO:8); Reaper, AVAFYIP (SEQ ID NO:9); Grim, AIAYFLP (SEQ ID NO:10); Hid, AVPFYLP (SEQ ID NO:11); hCasp-9, ATPFQEG (SEQ ID NO:12); mCasp-9, AVPYQEG (SEQ ID NO:13); xCasp-9, ATPVFSG (SEQ ID NO:14).

FIG. 2a, Stereo view of superimposition of the two structures from two different crystal forms. Smac and XIAP-BIR3 are colored green and orange, respectively. The bound Smac N-terminal peptide is shown in blue. The zinc atom is highlighted in red whereas its chelating residues are shown in yellow.

FIG. 2b, Schematic representation of the complete structure in one asymmetric unit. Two Smac protomers are colored green and blue, respectively. Two BIR3 domains are shown in orange and pink, respectively. Some secondary structural elements are labeled. In the crystals, each Smac protomer uses its extended N-terminus to bind a BIR3 domain whereas it interacts with a second BIR3 domain with a different interface. All figures are prepared with MOL-SCRIPT (Klaulis, *J. Appl. Crystallogr.* 24, 946–950, 1994) and GRASP (Nicholls et al., *Proteins: Struct. Funct. Genet.* 11, 281–296, 1991).

FIG. 3a, Overall view of the interaction between Smac N-terminal residues and XIAP-BIR3. Smac is colored blue and the interface residues from BIR3 are highlighted in yellow. The zinc atom is shown in red. The $2F_o$—$F_c$ electron density (omit map), shown in green, was contoured at $2.5\sigma$ and calculated with simulated annealing using XPLOR (Brunger, 1991, cited in Example 1) with the omission of the Smac N-terminal seven residues.

FIG. 3b, Close-up view of the binding groove on BIR3 for the Smac N-terminus. The blue and white colors represent the most and least hydrophobic surfaces, respectively. The N-terminal five residues of Smac are shown in green.

FIG. 3c, Close-up view of the interaction between the Smac N-terminus and the surface groove on BIR3. Smac and BIR3 are colored green and pink, respectively. Hydrogen bonds are represented by red dashed lines. Oxygen and nitrogen atoms are shown as red and blue balls, respectively.

FIG. 3d, Alignment of the N-terminal four amino acids of Smac (AVPI, SEQ ID NO:1) with those from the *Drosophila* proteins Hid (AVPF, SEQ ID NO:4), Grim (AIAY, SEQ ID NO:3), and Reaper (AVAF, SEQ ID NO:2).

FIG. 3e, Close-up view of a second interface between Smac and XIAP-BIR3. Smac and BIR3 are colored green and orange, respectively.

FIG. 4a, Caspase9-binding surface on XIAP-BIR3 overlaps with the Smac-binding groove. XIAP-BIR3 is primarily responsible for inhibiting caspase-9. Mutation of the three residues, W310, E314, and H343 (colored blue), abrogates caspase-9 inhibition by XIAP-BIR3. Four residues, T308, G305, G306, and P325, are shown in yellow. Mutation of the corresponding residues in the *Drosophila* protein DIAP1 (shown in parentheses) leads to a gain-of-function phenotype.

FIG. 4b, Proposed structure of a wild-type Smac/XIAP-BIR3 complex. Two perpendicular views are shown.

In FIG. 5d, the structures of DIAP1-BIR2 by itself and in complex with the Hid/Grim peptides are superimposed with that of XIAP-BIR3 in complex with the Smac tetra-peptide (PDB code 1G73). The DIAP1-BIR2 and XIAP-BIR3 are shown in cyan and purple, respectively. The bound Grim and Hid peptides are highlighted in orange and pink, respectively, while the Smac tetra-peptide is represented in green. Helix α6, highlighted in red, is only present in the peptide-bound BIR2.

FIG. 8a, Stereo view of the interface between DIAP1-BIR2, colored cyan, and the bound Grim peptide in orange. The important residues in DIAP1 are highlighted in yellow. Hydrogen bonds are represented by red dashed lines. The same DIAP1-BIR2 orientation is maintained for FIG. 12c.

FIG. 8b, Close-up view of the hydrophobic interface between DIAP1-BIR2 and the Grim peptide. The coloring scheme is the same as in panel A.

FIG. 8c, Stereo view of the interface between DIAP1-BIR2 and the bound Hid peptide, shown in pink.

FIG. 10a, Isothermal titration calorimetry for the interaction between DIAP1-BIR2 and the Hid peptide. The top part shows the actual titration data whereas the bottom part shows the curve fitting and the dissociation constant.

FIG. 10b, Dissociation constants for the binding of four different peptides to the BIR2 domain of DIAP1 and the BIR3 domain of XIAP. The estimated errors are approximately 15% for the tabulated values.

FIG. 13a, The amino acid sequences of Smac-5 (SEQ ID NO:24) and the NH$_2$-terminal sequence of Hid (SEQ ID NO:26), Reaper (SEQ ID NO:27) and Grim (SEQ ID NO:28) are shown. The conserved pentapeptide sequences are boxed.

FIG. 13b, 10–1000 μM of pentapeptides as indicated were assayed in a reaction containing recombinant human Apaf-1 and procaspase-9, XIAP, purified cytochrome c, and in vitro translated $^{35}$S-labeled procaspase-3. The procaspase-3 cleavage activity was measured by phosphorimaging.

DETAILED DESCRIPTION OF THE INVENTION

Figure 2:
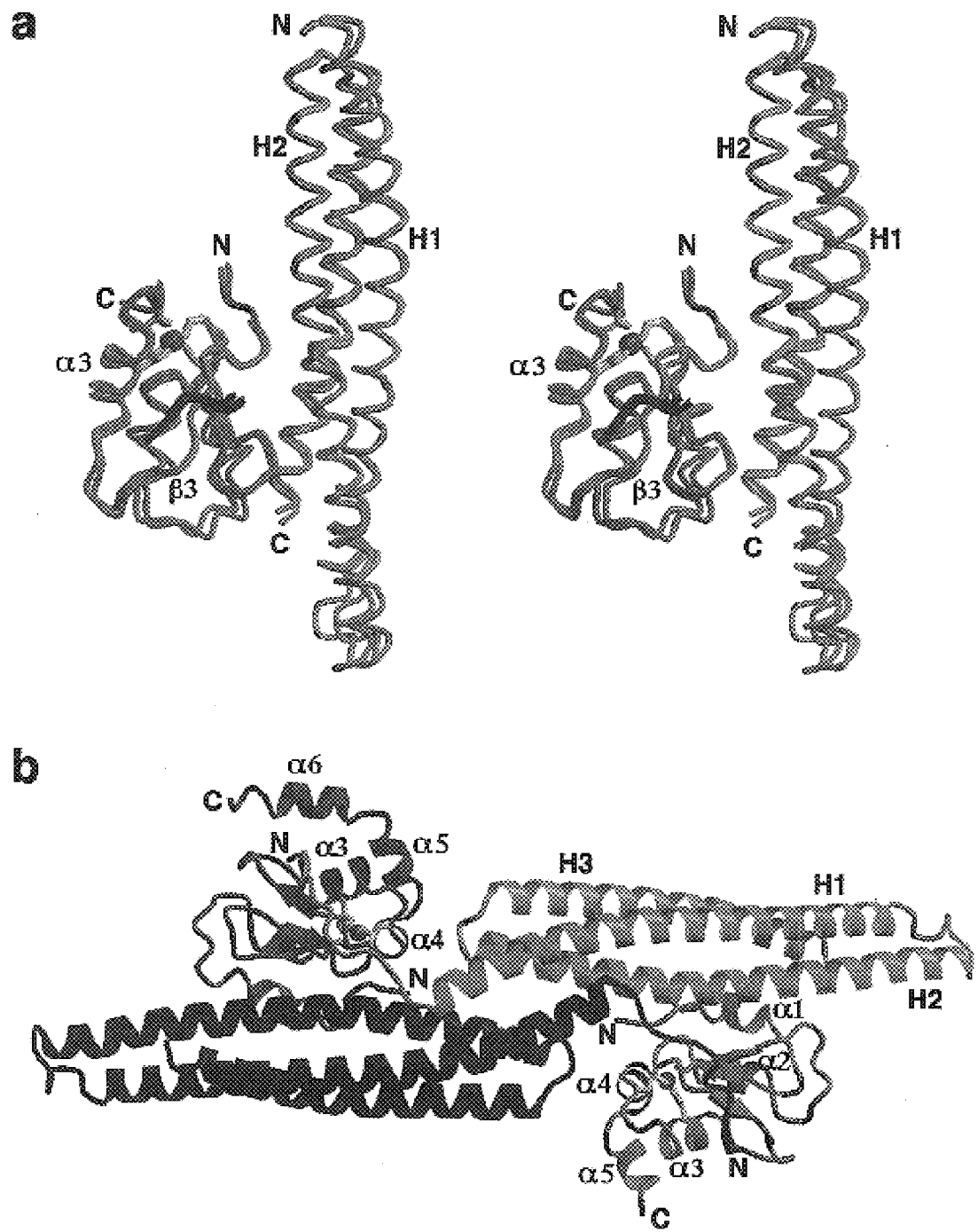
FIG. 2. Schematic representation of the Smac(Phe33Asp)/XIAP-BIR3 structures.

In accordance with the present invention, the specific structural basis for the recognition of and binding of Smac and its functional homologs to IAPs has been elucidated. The high-resolution crystal structure of Smac in complex with the third BIR domain (BIR3) of XIAP reveals that the amino-terminal four residues (Ala-Val-Pro-Ile; SEQ ID NO:1) in Smac recognize a conserved surface groove on BIR3, with the first residue Ala binding a hydrophobic pocket and making five hydrogen bonds to neighboring residues on BIR3. The amino acids that constitute this surface groove on XIAP-BIR3 are highly conserved among the BIR2 and BIR3 domains of c-IAP1, c-IAP2 and XIAP, and the single BIR domain of ML-IAP/Livin.

DIAP1 suppresses apoptosis in Drosophila, with the second BIR domain (BIR2) playing an important role. Three proteins, Hid, Grim, and Reaper, promote apoptosis, in part by binding to DIAP1 through their conserved N-terminal sequences. The crystal structures of DIAP1-BIR2 by itself and in complex with the N-terminal peptides from Hid and Grim reveal that these peptides bind a surface groove on DIAP1, with the first four amino acids mimicking the binding of the Smac tetra-peptide to XIAP. The next three residues also contribute to binding through hydrophobic interactions. Interestingly, peptide-binding induces the formation of an additional α-helix in DIAP1.

The aforementioned discoveries represent a novel and unexpectedly marked advance in the relevant art. Prior to these discoveries, it was unknown and unexpected that the N-terminal tetrapeptide of Smac and related IAP-BPs, in and of themselves, could relieve IAP-mediated inhibition of caspase activity. It had been known that an N-terminal 7-mer was capable of this function, but the evidence pointed to functionality of Ala at the N-terminal position rather than to the criticality of the N-terminal tetrapeptide itself, inasmuch as N 1–4 deletion mutants (exposing Ala at position 5) also retained binding activity (Chai et al., Nature 406, 855–862, 2000).

Of perhaps greater significance, prior to the discoveries of the present invention, the precise target on IAPs for binding of IAP-BPs was unknown. Certain evidence narrowed the target of Smac binding to BIR2 or BIR3 (Chai et al., 2000, supra), but no finer determination was available. By contrast, the present inventor has identified the precise binding groove in XIA1 BIR3 and DIAP1 BIR2, has structurally fine-mapped this binding groove, and has demonstrated that the residues involved in binding are highly evolutionarily conserved. This combination of discoveries, (1) the determination the the IAP-BP N-terminal tetrapeptide motif as the sufficient binding component and (2) the identification and characterization of the BIR binding groove, form the foundation of the present invention.

Other pro-apoptotic proteins bearing exposed AVPI-like sequences have been identified in accordance with the invention. For example the Drosophila Veto protein possesses the N-terminal sequence AIPF. Additionally, through sequence comparison, a Smac-like tetrapeptide (Ala$_{316}$-Thr$_{317}$-Pro$_{318}$-Phe$_{319}$, SEQ ID NO:5) was discovered in procaspase-9 (FIG. 1). The proteolytic cleavage that gives rise to the mature caspase-9 occurs after ASp$_{315}$, thus releasing this potential IAP-binding motif. Subsequent experiments confirmed that this tetrapeptide motif in the p12 subunit of caspase-9 is primarily responsible for the interactions with the BIR3 domain of XIAP (Srinivasula et al. Nature 409, 112–116, 2001). Therefore, unlike other caspases, proteolytic processing of procaspase-9 serves as a mechanism for both inhibition and activation. In the absence of proteolytic processing, XIAP is unable to interact with procaspase-9. Upon apoptotic stimuli, procaspase-9 undergoes auto-catalytic processing after ASp$_{315}$, exposing its internal tetrapeptide motif and resulting in the recruitment of and inhibition by XIAP. The release of the mature Smac from mitochondria presumably titrates XIAP, again using the same conserved N-terminal tetrapeptide in Smac. Thus, a conserved IAP-binding motif in caspase-9 and Smac mediates opposing effects on caspase activity and apoptosis. This fail-safe mechanism likely ensures protection against unwanted cell death resulting from accidental activation of caspases.

During apoptosis, the active caspase-9 can be further cleaved after Asp$_{330}$ by downstream caspases such as caspase-3. This positive feedback not only removes XIAP-mediated inhibition of caspase-9 but also releases a 15-residue peptide that is freely available to relieve IAP-mediated inhibition of other caspases. Thus, this peptide represents an endogenous drug timed to release by the apoptotic cells themselves to facilitate death.

Cancer cells express elevated levels of IAPs. For example, the majority of melanoma cell lines express high levels of Livin/ML-IAP compared to primary melanocytes. The human survivin gene is expressed in most common forms of cancer but not in terminally differentiated normal adult tissues. In addition to serving as caspase inhibitors, some of these IAPs exhibit intrinsic ubiquitin ligase activity (E3) and tag active caspases for proteasome-mediated degradation. These activities may significantly reduce or eliminate the effects of pro-apoptotic treatments such as chemotherapy. Thus removing the negative effects of these IAPs may represent a promising approach to sensitize cancer cells for apoptosis. Supporting this strategy, reduction in survivin expression by antisense RNA led to apoptosis and sensitization to treatment by anticancer drugs (Ambrosini et al. J. Biol. Chem. 273, 11177–11182, 1998). Given that the Smac-like tetrapeptide motif antagonizes IAP-mediated caspase inhibition, these peptides should also potentiate apoptosis in cells. Indeed, the inventor has observed that cells treated with the wild-type but not the mutant Smac tetrapeptide exhibited greater tendency to undergo apoptosis in response to UV radiation.

The analyses summarized above, and in greater detail below, shed light on the diversity and conservation of the TAP-binding peptides. It is now apparent that the first residue Ala1 plays an indispensable role in anchoring the peptide recognition of the BIR surface. There is a strong preference for Pro in the third position, particularly for binding to the mammalian protein XIAP. β-branched side chains appear to be necessary for the second position (Val, Thr, and Ile), while the fourth residue can tolerate Tyr or Ile but prefers Phe. Thus the optimal tetra-peptide is Ala1-Val2-Pro3-Phe4 for both DIAP1 and XIAP. Longer peptides derived from Hid or Grim do not improve the binding affinity to XIAP because the surface groove on the XIAP-BIR3 domain is optimized for tetra-peptide binding. However, in the *Drosophila* protein DIAP1, additional hydrophobic residues can significantly improve the binding affinity, especially if the third residue in the peptide is Ala. The N-terminal 7-residue peptide of Hid likely represents one optimal sequence for binding DIAP1.

Thus, the present invention in part is drawn to an evolutionarily conserved family of IAP-binding motifs, sometimes referred to herein as "IAP-binding peptides". The tetrapeptide motif present in proteins identified to date has the consensus sequence A-(V/T/I)-(P/A)-(F/Y/I/V) (SEQ ID NO:29), as shown in FIG. 1.

The IAP-binding peptide may be restricted to a tetrapeptide (sometimes referred to herein as "IAP-binding tetrapeptide" or "core tetrapeptide"), or it may also contain a consensus sequence comprising a fifth, sixth and seventh residue of the N-terminus. Based on peptides analyzed to date, this consensus sequence is (Y/F)-(L/I)-P.

The IAP-binding peptide may comprise conservative substitutions other than those shown in the consensus sequence of identified peptides. The table below sets forth features contributed by each residue at positions 1–4 (core tetrapeptide) and optional positions 5, 6 and 7. Positions 1–7 are referred to as X1-X7, respectively.

| Consensus sequence residue | Feature contributed by consensus sequence residue |
|---|---|
| X1 A | Anchors peptide recognition of BIR surface through (1) van der Waals interactions between its methyl side chain and conserved hydrophobic residues in BIR domain and (2) hydrogen bonds between its main chain groups and surrounding conserved polar residues in BIR domain. |
| X2 V, T, I | Van der Waals interactions between β-branched side chain and the generally conserved and hydrophobic groove on BIR domain. |
| X3 P, A | Ala is functional, but Pro is preferred in this position due to (1) stereochemistry of the groove on BIR domain and (2) better van der Waals packing between its cyclic side chain and the surrounding aromatic residues on BIR domain. |
| X4 F, Y, I, V | Van der Waals interaction with conserved surface groove on BIR domain |
| X5 Y, F | Unique to DIAP1 and its binding groove homologs, van der Waals contacts. |
| X6 L, I | Unique to DIAP1 and it s binding groove homologs, van der Waals contacts. |

-continued

| Consensus sequence residue | Feature contributed by consensus sequence residue |
|---|---|
| X7 P | Unique to DIAP1 and its binding groove homologs, van der Waals contacts. |

Thus, the core IAP-binding tetrapeptide has the following general features:

1) a backbone conformation comprising an extended strand/turn.

2) at position X1, (1) van der Waals interactions with the BIR3 binding pocket comprising van der Waals interactions between a nonpolar (e.g., methyl) side chain and conserved residues in the BIR domain and (2) hydrogen bonds between the main chain groups and surrounding conserved polar residues in BIR domain;

3) at position X2, van der Waals interactions between the side chain and hydrophobic groove on BIR domain;

4) at position X3, stereochemistry of fit into the groove of BIR domain and van der Waals packing into surrounding aromatic residues on BIR domain;

5) at position X4, van der Waals interaction with conserved surface groove on BIR domain.

6) If the IAP-binding peptide is supplemented with residues 5–7, each of positions X5, X6 and X7 supplies additional van der Waals interactions with hydrophobic components of the BIR surface groove (applies to the BIR2 of DIAP1 and its structural homologs).

Further details of the intermolecular forces involved in recognition and binding of IAP-binding peptides to IAPs are set forth in Examples 1–3 below. In addition, FIGS. 1–10 show the relevant structural interactions, as well as alignments of evolutionarily conserved regions of IAPs involved in the surface groove recognized by the IAP-binding peptides.

IAP-binding peptides are conveniently prepared by chemical peptide synthesis, according to standard methods. Following synthesis, the peptides are purified, e.g., by reverse-phase HPLC, and lyophilized.

Knowing these precise structural features of naturally-occurring IAP-binding peptides, it is advantageous, and well within the level of skill in this art, to design peptidomimetics that have an equivalent structure or function. Such mimetics are another feature of the present invention. Mimetics of the core IAP-binding tetrapeptides are preferred in this aspect of the invention. The tetrapeptide is suitably small, and its structural features in relation to the IAP binding groove are well characterized, thereby enabling the synthesis of a wide variety of mimetic compounds. Added advantages of compounds of this size include improved solubility in aqueous solution and ease of delivery to selected targets in vivo.

The terms "mimetic", peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

In one embodiment, the IAP-binding peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from 5 members to 4, 6, or 7 members. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, *Ann. Rep. Med. Chem.* 24, 243–252, 1989). Certain peptidomimetic compounds are based upon the amino acid sequence of the peptides of the invention. Often, peptidomimetic compounds are synthetic compounds having a three-dimensional structure (i.e. a "peptide motif") based upon the three-dimensional structure of a selected peptide. The peptide motif provides the peptidomimetic compound with the desired biological activity, i.e., binding to IAP, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, *Curr. Op. Chem. Biol.* 2, 441–452, 1998; Hruby et al., *Curr. Op. Chem. Biol.* 1, 114–119, 1997; Hruby & Balse, *Curr. Med. Chem.* 9, 945–970, 2000). One class of peptidomimetics a backbone that is partially or completely non-peptide, but mimics the peptide backbone atom-for atum and comprises side groups that likewise mimic the functionality of the side groups of the native amino acid residues. Several types of chemical bonds, e.g. ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

It has been demonstrated in accordance with the present invention that the IAP-binding tetrapeptides are capable of potentiating apoptosis of cells. Accordingly, another aspect of the present invention is a method of stimulating apoptosis in a cell, which comprises administering to the cell an amount of an IAP-binding peptide effective to stimulate apoptosis in the cell. In one embodiment, the cell is a cultured cell. In another embodiment, the cell is contained within a tissue, and the tissue preferably is located within a living organism, preferably an animal, more preferably a mammal, and most preferably a human. These latter embodiments are carried out by formulating the IAP-binding peptides of the invention as a pharmaceutical preparation for administration to a subject. Such a pharmaceutical preparation constitutes another aspect of the present invention.

In another aspect of the present invention, the IAP-binding peptides are utilized in various assays to screen for and identify compounds capable of acting as agonists or antagonists of the IAP-IAP binding protein interactions within cells. Agonists of this interaction are expected to be useful as pro-apoptotic drugs for treatment of cell proliferative diseases such as cancer. Antagonists of this interaction are expected to be useful as anti-apoptotic drugs for treatment of diseases where inhibition of apoptosis is needed, e.g., Alzheimer's disease, stroke and arthritis, to name a few.

In a preferred embodiment of the invention, the IAP-binding peptides are used in a cell-free binding assay to screen for IAP-binding agonists or antagonists. Such assays are well known to persons of skill in the art, and are particularly useful for high throughput screening of candidate drugs, e.g., from a chemical library or produced by rational drug design (mimetics) as described above.

In a typical binding assay, an IAP-binding peptide of known binding affinity to a binding partner, i.e., an IAP, is incubated with that IAP in the presence or absence of a test compound suspected of being capable of binding IAP. The assay is constructed such that a change in the ability of the IAP-binding peptide to bind IAP (presumably due to the activity of the test compound) is detectable. If such change is detected in the presence of the test compound, this is indicative that the test compound is capable of binding IAP, and therefore may act either as an agonist or antagonist of native IAP-binding proteins in the cell.

In another embodiment of the invention, the ability of a candidate drug to simulate or inhibit apoptosis is tested in a cell-free activity assay of downstream targets of IAP. In the absence of an IAP-binding protein, IAP itself interacts with and inhibits activity of caspases, thereby arresting apoptosis. Such assays include, but are not limited to, direct caspase-9 activity assays and caspase activation assays (cleavage of procaspases), as exemplified herein. In these assays, an IAP-binding peptide of the invention, having a pre-determined level of activity in such assays, is used as a positive control and, optionally, a corresponding peptide known not to be active in the assay (e.g., a peptide deleted or replaced at the N-terminal Alanine) is used as a negative control. Assays are conducted using these controls, and selected test compounds are tested for their ability to (1) relieve inhibition of a caspase by IAP, or (2) to stimulate such inhibition.

In another embodiment of the invention, the ability of a candidate drug to stimulate or inhibit apoptosis in a cultured cell is tested, according to standard methods. In these assays, an IAP-binding peptide of the invention, having a predetermined level of activity in such assays, is used as a positive control and, optionally, a corresponding peptide known not to be active in the assay (e.g., a peptide deleted or replaced at the N-terminal Alanine) is used as a negative control. Assays are conducted using these controls, and selected test compounds are tested for their ability to stimulate or inhibit apoptosis. The cells that undergo apoptosis can be differentiated from normal cells by distinct morphological changes or by molecular markers, such as cleavage of chromosomes into nucleosome ladders (detected by nuclear DNA staining).

The following examples are provided to describe the invention in greater detail. They are intended to illustrate, not to limit, the invention.

EXAMPLE 1

Structural Basis of IAP Recognition by Smac

All members of the IAP family contain at least one BIR (baculoviral IAP repeat) motif and many contain three. Recent experiments indicate that different BIR domains may exhibit distinct functions. The second BIR domain (BIR2) of XIAP is a potent inhibitor for caspase-3 whereas XIAP-BIR3 primarily targets the active caspase-9. Smac is synthesized as a precursor molecule of 239 amino acids; the N-terminal 55 residues serve as the mitochondria targeting sequence that is removed after import. The wild-type Smac protein (residues 1–184) forms a dimer in solution and interacts with both the BIR2 and BIR3 domains of XIAP. Point mutations at the dimeric interface, such as Phe33Asp, completely inactivate dimer formation. Such monomeric mutants can no longer interact with XIAP-BIR2; but they retain binding to the BIR3 domain. A missense mutation of the N-terminal Ala residue to Met (Ala1Met) in wild-type Smac abolishes binding to both the BIR2 and BIR3 domains of XIAP and results in complete loss of Smac function. In support of its critical role, a short 7-residue peptide derived from the Smac N-terminus was able to promote the activation of procaspase-3.

To provide a structural basis for IAP recognition by Smac, the wild-type Smac was crystallized in complex with either the BIR2 or the BIR3 domain of XIAP. But these crystals did not diffract x-rays well. To facilitate crystallization, binary complexes were reconstituted using a monomeric Smac protein (with the missense mutation Phe33Asp). Crystals of this mutant Smac with XIAP-BIR3 (residues 238–358) were obtained in two different conditions, neither of which disrupted interactions between Smac and XIAP-BIR3 in solution. These two crystal structures of the binary complex have been determined at 2.0 and 2.6 Å, respectively.

Methods

Site-directed mutagenesis and protein preparation. Point mutations were generated by PCR, and the identities of individual clones were verified by sequencing. Recombinant XIAP-BIR3 (residues 238–358) were overexpressed as GST-fusion proteins using pGEX-2T (Pharmacia). The mutant Smac protein (Phe33Asp, residues 1–162) was overexpressed in *Escherichia coli* strain BL21(DE3) using a pET-3d vector (Novagen). Selenomethionyl Smac (Phe33Asp) was expressed in *E. coli* B834(DE3) (Novagen) in M9 minimal medium supplemented with 50 mg/l selenomethionine. Protein purification was performed as described (Chai et al., *Nature* 406, 855–862, 2000). The concentration of the final complex was approximately 15 mg/ml. For interaction assays, both wild-type and mutant Smac were overexpressed in *Escherichia coli* strain BL21 (DE3) as C-terminally 9-Histidine-tagged proteins using a pET-15b vector (Novagen).

In vitro interaction assay. Interaction between Smac and XIAP-BIR3 was examined by GST-mediated pull-down assays. Approximately 0.4 mg of a wild-type or mutant BIR3 fragment was bound to 200 µl of glutathione resin as a GST-fusion protein and incubated with 0.5 mg of wild-type or mutant Smac at room temperature. After extensive washing with an assay buffer containing 25 mM Tris, pH 8.0, 150 mM NaCl, and 2 mM dithiothreitol (DTT), the complex was eluted with 5 mM reduced glutathione and visualized by SDS-polyacrylamide gel electrophoresis (SDS-PAGE) with Coomassie staining.

Crystallization and data collection. Crystals were grown by the hanging-drop vapor-diffusion method by mixing the Smac/XIAP-BIR3 complex (15 mg/ml) with an equal volume of reservoir solution. At 4° C., the reservoir contained 100 mM MES buffer, pH 6.5, 12% isopropanol (v/v), 200 mM sodium citrate, and 10 mM DTT. At 23° C., the reservoir contained 100 mM citrate buffer, pH 5.5, 5% PEG 4000, and 10% isopropanol. Crystals appeared after 1–4 days and reached a maximum size over a period of 1–3 weeks. Both crystals are in the triclinic space group P1 and contain two complexes in each unit cell. However, the unit cell dimensions are significantly different. Crystals grown at 4° C. have a=47.0 Å, b=54.6 Å, c=74.2 Å, α=93.0, β=101.1, and γ=94.9; crystals grown at 23° C. have a=48.1 Å, b=52.9 Å, c=67.1 Å, α=100.0, β=104.1, and γ=94.0. Diffraction data were primarily collected using an R-AXIS-IV imaging plate detector mounted on a Rigaku 200HB generator. Derivatives were obtained by soaking crystals in reservoir buffer containing 20% glycerol (v/v) and heavy atoms. The concentration and soaking time for mercury thimerosal were 1 mM and 20 hours, respectively. To collect data at −170° C., crystals were equilibrated in a cryoprotectant buffer containing reservoir buffer plus 20% glycerol (v/v) and were flash frozen in a cold nitrogen stream. The high-resolution native data were collected at the NSLS beamline X4A.

Structure determination. The crystals grown at 4° C. were analyzed first, because of the availability of a high-quality selenomethionine derivative. The first six selenium positions were determined using SOLVE (Terwilliger et al., *Acta Crystallogr*. D52, 749–757, 1996) and further refined using MLPHARE (Collaborative Computational Project, N. The CCP4 Suite: Programs for Protein Crystallography. *Acta Crystallogr*. D50, 760–763, 1994). The positions of the other four selenium atoms and mercury thimerosal were identified using difference Fourier methods. Initial MIR phases calculated with the program MLPHARE had a mean figure of merit of 0.404 to 3.0 Å resolution, and were improved with solvent flattening and histogram matching using the program DM (Collaborative Computational Project, N., 1994, supra). The electron density for the Smac N-terminal four residues was very clear in the experimental map. A model was built into MIR electron density with the program 0 (Jones et al., *Acta Crystallogr*. A47, 110–119, 1991) and refined at 2.6 Å resolution by simulated annealing using the program XPLOR (Brunger, A. T., *X-PLOR, a System for Crystallography and NMR*, Yale University Press, New Haven, Conn., 1991). Non-crystallography symmetry (NCS) constraints were applied to all refinement cycles except the last one. The two refined complexes (R factor 24% and free R 28.5%) are nearly identical to one another, and contain Smac residues 1–6 and 13–157, XIAP residues 251–343, and 58 ordered water molecules. Residues 7–12 and 158–162 in Smac and the terminal residues in XIAP (238–250 and 344–358) have no electron density in the maps, and it is presumed that these regions are disordered in the crystals. After completion of the refinement for the crystals grown at 4° C., the atomic coordinates of BIR3 and Smac were used individually to obtain molecular replacement solutions for the crystals grown at 23° C., using AmoRe (Navaza, J., *Acta Crystallogr* A50, 157–163, 1994). The solutions were combined in 0. Rigid body refinement by XPLOR confirmed the correctness of the solutions. This model was further refined at 2.0 Å resolution by simulated annealing using the program XPLOR, followed by model building in 0. NCS was helpful for the initial cycles of refinement. The final refined model, with an R factor of 22.7% and free R of 26.8%, contains two complexes. One complex contains Smac 1–157 and XIAP256–357, and the other complex contains Smac 1–157 and XIAP256–343. Except for the C-terminal 14 residues of XIAP in the first complex, which is disordered in the second one, the structures of these two complexes are identical to one another.

Cys327) (FIG. 2). The XIAP-BIR3 structure closely resemble those of other BIR domains, with approximately 1.22 and 1.38 Å RMSD to the aligned Cα atoms of survivin and cIAP1-BIR2, respectively. In the crystals, Smac recognizes XIAP-BIR3 with two interfaces. First, the N-terminal four residues in Smac, Ala1-Val2-Pro3-Ile4, bind a surface groove on BIR3 formed by the strand β3, the helix α3, and the intervening loop. Two of these four residues, Val2 and Pro3, form a short anti-parallel β-strand with the three-stranded β-sheet of BIR3 (FIGS. 2*a* & 3*a*). Second, the helices H2 and H3 in Smac contact the BIR3 residues surrounding the helix α1 (FIG. 2*a*). Interestingly, the N-terminal residues and the H2-H3 helices in Smac that contact the same BIR3 domain are from two different Smac protomers (FIG. 2*b*). The N-terminus of one Smac protomer extends out and recognizes a BIR3 domain that interacts with another Smac protomer through the second interface (FIG. 2*b*). This arrangement is in agreement with the inventor's structure-based prediction (Chai et al., 2000, supra).

TABLE 3

Data collection and statistics from the crystallographic analysis

|  | Native (1) | Se-Met (1) | Thimerosal (1) | Native (2) |
| --- | --- | --- | --- | --- |
| Data set (X4A) |  |  |  |  |
| Space group | P1 |  |  | P1 |
| Unit cell dimension | 47, 55, 74, 93, 101, 95 |  |  | 48, 52, 67, 100, 104, 94 |
| Resolution (Å) | 99.0–2.6 | 99.0–2.5 | 99.0–3.0 | 99.0–2.0 |
| Total observations | 82,274 | 89,626 | 51,549 | 172,837 |
| Unique observations | 21,546 | 23,635 | 14,087 | 40,346 |
| Data coverage (outer shell) | 96.8% (95.4%) | 93.6% (68.2%) | 97.0% (93.4%) | 94.8% (88.5%) |
| $R_{sym}$ (outer shell) | 0.054 (0.271) | 0.058 (0.223) | 0.094 (0.365) | 0.045 (0.270) |
| MIR analysis (20–3.5 Å) |  |  |  |  |
| Heavy atom sites |  | 10 | 8 |  |
| Isomorphous difference (outer shell) |  | 0.120 (0.143) | 0.372 (0.433) |  |
| Phasing power |  | 1.75 | 1.21 |  |
| Cullis R factor |  | 0.67 | 0.83 |  |
| Overall Figure-of-Merit |  | 0.4036 |  |  |
| Refinement |  |  |  |  |
| Resolution range (Å) | 20.0–2.6 |  |  | 20.0–2.0 |
| $R_{working}/R_{free}$ | 24.2%/28.7% |  |  | 22.7%/26.8% |
| Number of atoms | 3792 |  |  | 4263 |
| Number of waters | 116 |  |  | 249 |
| R.m.s.d. bond length (Å) | 0.008 |  |  | 0.010 |
| R.m.s.d. bond angles (degree) | 0.963 |  |  | 1.395 |
| R.m.s.d. B-factors | 3.466 |  |  | 2.97 |

$R_{sym} = \Sigma_h \Sigma_i |I_{h,i} - I_h| / \Sigma_h \Sigma_i I_{h,i}$, where $I_h$ is the mean intensity of the i obervations of symmetry related reflections of h. $R = \Sigma |F_{obs} - F_{calc}| / \Sigma F_{obs}$, where $F_{obs} = F_P$, and $F_{calc}$ is the calculated protein structure factor from the atomic model ($R_{free}$ was calculated with 5% of the reflections). R.m.s.d. in bond lengths and angles are the deviations from ideal values, and the r.m.s.d. deviation in B factors is calculated between bonded atoms.

Results

The two crystal structures of the binary complexes of Smac with XIAP-BIR3 were determined at 2.0 and 2.6 Å, respectively. There are two identical complexes in each asymmetric unit in each of the two crystal forms. Although the packing interactions are different, two sets of conserved interaction interfaces between Smac and XIAP-BIR3 are present in these two crystal forms, with 0.95 Å root-mean-square-deviation (RMSD) for all aligned Cα atoms (FIG. 2*a*). Because of these conserved features, the discussion below is limited to the 2.0 Å structure (FIG. 2*b*).

In the complex, the Smac protomer is an elongated three-helix bundle (FIG. 2), very similar to the structure of Smac by itself (0.7 Å RMSD for aligned Cα atoms; Chai et al., 2000, supra). XIAP-BIR3 consists of six α-helices, a three-stranded β-sheet, and a zinc atom chelated by three Cys and one His residues (Cys300, Cys303, His320, and The N-terminal four residues of Smac pack into a surface groove on XIAP-BIR3, resulting in the burial of 892 Å$^2$ exposed surface area (FIG. 3*b*). The recognition specificity is achieved through a combination of hydrogen bond interactions and van der Waals contacts (FIG. 3*a*). A total of eight inter- and three intra-molecular hydrogen bonds support the binding of the Smac tetrapeptide (Ala1-Val2-Pro3-Ile4) in the surface groove on BIR3. Three intermolecular contacts between the backbone groups of Val2/Ile4 in Smac and Gly306/Thr308 in BIR3 allow the formation of a 4-stranded antiparallel β-sheet (FIG. 3*c*). The remaining hydrogen bonds constitute an intricate network surrounding the N-terminal residue Ala1. At the center of the network, the amino group of Ala1 donates three hydrogen bonds to Glu314 and Gln319 whereas its carbonyl group makes two additional contacts to Gln319 and Trp323 (FIG. 3*c*). At the periphery of the network, three intra-molecular contacts further buttress the interactions (FIG. 3*c*).

In addition to the hydrogen bond network, van der Waals contacts also appear to play an important role in stabilizing the interactions between the Smac tetrapeptide and the BIR3 surface groove. The methyl group of Ala1 fits tightly in a hydrophobic pocket formed by the side chains of Leu307, Trp310, and Gln319 (FIG. 3c). Stereochemical parameters indicate that replacement of Ala1 by any other residue except Gly will cause steric hindrance in this pocket, likely weakening binding and abolishing hydrogen bonds by the amino and carbonyl groups of Ala1. This observation explains the finding that the mutation Ala1Met in Smac completely eliminated interaction with the BIR domains (Chai et al., 2000, supra). The absolute requirement for Ala as the N-terminal residue is also consistent with the observation that the mutant Smac-del4 retained weak interaction with the BIR domains (Chai et al., 2000, supra), as removal of the first four residues in Smac leaves Ala5 as the N-terminal residue. It is predicted that Ala1 cannot be replaced by Gly because of the associated entropic penalty and loss of van der Waals interactions.

The bulky, flat aromatic side chain of Trp323 plays a major role in forming the surface groove on BIR3 (FIG. 3c). Both Val2 and Pro3 maintain multiple van der Waals interactions with Trp323, while Pro3 makes additional contact to Tyr324 (FIG. 3c). In addition, the side chain of Ile4 interacts with Leu292, Gly306, and the aliphatic side chains of Lys297 and Lys299. Of these residues, Gly306 appears to be particularly important, because the absence of a side chain at this position makes these interactions possible (FIG. 3c). Although Ala5 and Gln6 in Smac are ordered in the crystals, they do not make important interactions to the BIR3 domain; nor are they involved in binding the surface groove.

Among the amino-terminal four residues, Ala1 makes the largest contribution to the specific recognition of XIAP. The next three residues, Val2, Pro3, and Ile4, are all hydrophobic, and they interact with the hydrophobic residues lining the BIR3 surface groove. These residues also contribute to the appropriate positioning of Ala1 in the pocket (FIG. 3c); however, their identity does not appear to be as critical as that of the N-terminal Ala1.

The foregoing structural analysis has identified several residues in XIAP-BIR3 that mediate key interactions with Smac. To confirm these structural observations, nine missense mutations on BIR3 were created and their interaction with Smac were examined, using purified recombinant proteins. Consistent with their important roles in binding the Smac N-terminus, point mutation to Ala or Arg for any of the three residues Glu314, Gln319, and Trp323 significantly reduced or abolished interaction with the wild-type Smac protein, presumably because of the disruption of binding to the Smac tetrapeptide (data not shown). In contrast, three control mutations outside the peptide-binding surface, Glu282Ala, Glu282Arg, and Arg286Glu, had no detectable effect on the interaction between XIAP-BIR3 and Smac (data not shown).

In *Drosophila*, three proteins, Hid, Grim, and Reaper, appear to be the functional homologues of the mammalian Smac. These three proteins appear to act upstream of the *Drosophila* IAP, DIAP1, and physically interact with DIAP1 to relieve its inhibitory effect on caspase activation. Although previous sequence alignment between Smac and the *Drosophila* proteins failed to reveal significant homology, the revelation of a Smac tetrapeptide binding to XIAP motivated us to re-examine the N-terminal sequences of Hid/Grim/Reaper. This analysis revealed striking similarity in the N-termini of these proteins (FIG. 3d). All three *Drosophila* proteins begin with Ala; both Reaper and Hid have Val in the second position whereas Grim replaces Val with a conserved Ile. This sequence conservation strongly suggests that the *Drosophila* proteins Hid/Grim/Reaper may interact with DIAP1 in a similar fashion and that the N-terminal sequences from Hid/Grim/Reaper may recognize the same surface groove. This analysis also predicts that (1) the initiating Met residue in Hid/Grim/Reaper is removed by a methionyl peptidase in *Drosophila* as is the case in *E. coli*, and (2) other pro-apoptotic proteins bearing N-terminal homology to the Ala-Val-Pro-Ile sequence may remain to be discovered.

In addition to the peptide-binding groove, a second interaction interface between Smac and the BIR3 domain of XIAP was observed (FIG. 3e). Residues around the helix α1 in BIR3 pack against the middle portion of helices H2 and H3 in Smac. This interface consists of seven hydrogen bonds and two patches of van der Waals interactions, with over 2000 Å$^2$ buried surface area (FIG. 3e). The hydrogen bonds cluster in a small area, where Glu99 and Thr100 in Smac make six contacts to Asn259, Ser261, and Arg258 (FIG. 3e). In addition, Arg85 on helix H2 donates one hydrogen bond to the side chain of Thr274 (FIG. 3e). Although van der Waals interactions scatter throughout the large interface (FIG. 3e), there are two prominent patches. First, Phe270 on helix α1 of XIAP-BIR3 extends out into a hydrophobic pocket formed by the side chains of Met88, Leu153, Ala154, Gln157 and Glu150 (FIG. 3e). Second, Leu96 on helix H2 makes multiple contacts to the side chains of Met262 and Tyr290 (FIG. 3e). Although the buried surface area is relatively large for this interaction interface, shape complementarity between Smac and BIR3 is not optimal. Compared to the binding of the Smac N-terminal tetrapeptide to the surface groove on BIR3, this interface is likely to play a minor role. This analysis is consistent with the observation that N-terminal deletion mutants of Smac failed to bind XIAP-BIR3 (Chai et al., 2000, supra).

Wild-type Smac interacts with the BIR2 and BIR3 of XIAP but does not bind the BIR1 domain (Chai et al., 2000, supra). To explain this observation, the primary sequences of the BIR domains from XIAP and cIAP-1 were compared. Among the many residues that line the BIR3 surface groove, five appear to be mediating critical contacts with Smac. Leu307 and Trp310 are involved in pocket formation for the side chain of Ala1 of Smac; Glu314 hydrogen bonds to Ala1; Trp323 interacts with Val2 and Pro3 and hydrogen bonds to Ala1; Gly306 allows docking of Ile4. Among these five residues, Trp310 is invariant; Leu307 and Glu314 are highly conserved among all BIR domains. The replacement of Gly306 by other residues in BIR2 and BIR1 likely disrupts tight packing of Ile4 of Smac against residues in the BIR domain. More importantly, Trp323 is replaced by His in the BIR2 domain and Val/Leu in the BIR1 domain, which may alter the lining of the surface groove. The replacement of Trp323 by His in BIR2 is likely to be less deleterious than by Val/Leu because His may retain the hydrogen bond contact to the carbonyl group of Ala1 in Smac (FIG. 3c). These analyses are consistent with the observations that wild-type Smac does not interact with BIR1 and that monomeric Smac mutants fail to bind BIR2.

The BIR3 domain of XIAP is primarily responsible for the inhibition of caspase-9 activity. How does Smac relieve this inhibition? Both published observations and current analysis suggest a model of mutual exclusion of caspase-9 and Smac for binding to the BIR3 domain. Three mutations in XIAP-BIR3, Glu314Ser, Trp310Ala, and His343Ala, abolish inhibition of caspase-9 activity (Sun et al., *J. Biol. Chem.* 275, 33777–33781, 2000), suggesting that the affected residues may directly contact caspase-9 and inhibit its activity. Indeed, the three affected residues are close to each other and two of them are directly involved in binding Smac tetrapeptide (FIG. 4a). In the structure, Trp310 forms an important part of the pocket that accommodates Ala1 in Smac, suggesting that binding by the Smac N-terminus may evict a binding moiety of caspase-9 from the pocket. In addition, the amino group of Ala1 in Smac makes a pair of charge-stabilized hydrogen bonds to the side chain of Glu314 in XIAP, likely competing with the interaction between Glu314 and caspase-9. His343Ala affects a residue that abuts the peptide-binding pocket, further supporting the mutual exclusion model (FIG. 4a).

The foregoing structural analysis also provides a plausible explanation for gain-of-function (GOF) mutations in DIAP1. All five reported GOF mutations (Goyal et al., *EMBO J.* 19, 589–597, 2000; Lisi et al., *Genetics* 154, 669–678, 2000) appear to disrupt the peptide-binding groove and impair binding by the *Drosophila* proteins Hid/Grim/Reaper (FIG. 4a). For example, Gly269Ser affects a residue that corresponds to G306 in XIAP-BIR3; Val85Met and Gly88Asp (or Gly88Ser) affect residues that correspond to Gly305 and Thr308 in XIAP, respectively. These residues are either in the groove (Gly306 & Thr308) or in the vicinity of the groove (Gly305). The fifth GOF mutation, Pro105Ser, affects a corresponding residue (Pro325) in XIAP that makes a sharp turn and allows Trp323 to line the groove. The inventor suggests that these five mutations impair binding of DIAP-1 to Hid/Grim/Reaper without significantly affecting binding to *Drosophila* caspases (FIG. 4a).

Although a Smac monomeric mutant (Phe33Asp) was used for crystallization, there are two complexes in each asymmetric unit in the crystals (FIG. 2b). Interestingly, the two Smac protomers pack against each other using part of the wild-type dimeric interface (FIG. 2b). Docking the XIAP-BIR3 domain onto the wild-type Smac dimer structure using the BIR3:Smac interface observed here places the BIR3 domain underneath the arch-shaped Smac molecule (FIG. 4b). Intriguingly, this arrangement also places two BIR3 domains next to each other (FIG. 4b). This model for the complex between wild-type Smac and BIR3 is consistent with available biochemical data. For example, XIAP-BIR2 does not interact with the monomeric mutants of Smac, suggesting that BIR2:BIR2 interactions may be required for stable binding of BIR2 to the wild-type dimeric Smac.

In summary, high-resolution crystal structure of a complex between Smac and the BIR3 domain of XIAP reveals a peptide binding groove on the surface of BIR3 which plays an important role in IAP function. The peptide-binding groove is lined with both hydrophobic and negatively charged residues and appears to be a promising drug target. Future experiments should be directed at identification and optimization of a high-affinity drug that is capable of promoting apoptosis in cancer cells.

EXAMPLE 2

Structural Analysis of a Functional DIAP1 Fragment Bound to Grim and Hid Peptides The Inhibitor of Apoptosis protein DIAP1 suppresses apoptosis in *Drosophila*, with the second BIR domain (BIR2) playing an important role. Three proteins, Hid, Grim, and Reaper, promote apoptosis, in part by binding to DIAP1. Although Hid, Grim and Reaper perform a similar function in promoting cell death, they only share homology in the N-terminal 14 residues of their primary sequences (Chen et al., *Genes Devel.* 10, 1773–1782, 1996). These N-terminal sequences are sufficient to mediate interactions with DIAP1 (Vucic et al., *Proc. Natl. Acad. Sci. USA* 94, 10183–10188, 1998) and with several mammalian IAPs (McCarthy and Dixit, *J. Biol. Chem.* 273, 24009–24015, 1998). In the case of Hid in insects, and Hid and Reaper in mammalian cells, these N-terminal sequences are essential for pro-apoptotic function.

To investigate the structural mechanisms of DIAP1 recognition by the *Drosophila* Hid, Grim and Reaper proteins, the DIAP1-BIR2 domain has been crystallized by itself and in complex with the N-terminal peptides from both Hid and Grim and determined these structures at 2.7, 2.7, and 1.9 Å resolution, respectively. This example describes those results.

Methods

Protein and peptide preparation. All constructs were generated using a standard PCR-based cloning strategy, and the identities of individual clones were verified through double-stranded plasmid sequencing. Recombinant DIAP1-BIR1 (residues 1–145) and BIR2 (residues 201–325) were overexpressed as GST-fusion proteins using pGEX-2T (Pharmacia). The soluble fraction of the GST-DIAP1 fusion in the *E. coli* lysate was purified over a glutathione sepharose column, and further purified by anion-exchange chromatography (Source-15Q, Pharmacia). The GST moiety was removed by thrombin cleavage, and the resulting BIR domain was further purified by gel filtration (Superdex-200, Pharmacia). The 10-residue Hid and Grim peptides were chemically synthesized, purified by reverse phase HPLC, and lyophilized. The homogeneous DIAP1-BIR2 domain was mixed with equi-molar amount of synthetic peptide and diluted to a final concentration of 10 mg/ml.

Crystallization and data collection. Crystals for DIAP1-BIR2 by itself were grown by the hanging-drop vapor-diffusion method by mixing the protein (10 mg/ml) with an equal volume of reservoir solution containing 100 mM Tris, pH 8.0, 60% 2, 4-methyl-pentane-diol (v/v), and 10 mM DTT. Crystals, with a typical dimension of 0.2×0.2×0.08 mm$^3$, are in the spacegroup I4 and contain two molecules in each asymmetric unit. The unit cell dimensions are a=b=96.1 Å, and c=59.3 Å. Crystals of DIAP1-BIR2 in complex with the Hid peptide were grown by the hanging-drop vapor-diffusion method by mixing the complex (10 mg/ml) with an equal volume of reservoir solution containing 100 mM Tris, pH 8.5, 1.4 M $NH_4H_2PO_4$, and 10 mM DTT. Multiple crystals appeared overnight in the midst of heavy precipitation. Macroseeding yielded crystals with a maximum size of 0.2×0.2×0.4 mm$^3$ over a period of 6–7 days. The crystals are in the primitive hexagonal space group $P6_522$, with unit cell dimensions a=b=62.7 Å, c=130.7 Å. The BIR2-Grim crystals were obtained using tiny BIR2-Hid crystals as micro-seeds and grew to a much larger size. The unit cell dimensions are very similar to the BIR2-Hid crystals. Diffraction data were collected using an R-AXIS-IV imaging plate detector mounted on a Rigaku 200HB generator. For all data sets, crystals were equilibrated in a cryoprotectant buffer containing well buffer plus 20% glycerol, and were flash frozen in a −170° C. nitrogen stream.

Structure determination. The structure of DIAP1-BIR2 by itself was determined by Molecular Replacement, using the software AMORE(Navaza, 1994, supra). The atomic coordinates of the XIAP-BIR3 domain (PDB code 1G73) was used for rotational research against the 12–3.0 Å data set. The top 50 solutions from the rotational search were individually used for a subsequent translational search, which yielded two promising solutions with correlation factors of 23–24 and R-factors of 52–53%. These two solutions turn out to be the two molecules in each asymmetric unit in the crystals; together, they give a combined correlation factor of 36.5 and an R-factor of 46%. The peptide-bound BIR2 structures were solved using the partially refined BIR2 structure as the initial search model. All solutions were examined with the program O (Jones et al., 1991, supra). Refinement by the program XPLOR (Brunger, 1991, supra) quickly reduced the R-factor and R-free to the ranges of 28-32% and 31–35%, respectively. The electron density for the bound peptide fragments became clear and unambiguous. A model was built with the program O and refined further by simulated annealing using XPLOR. For DIAP1-BIR2 by itself, the final refined atomic model contains residues 215–310 and 18 ordered water molecules at 2.7 Å resolution. For DIAP-BIR2 in complex with the Grim peptide, the final model contains residues 214–318 from DIAP1, the N-terminal 8 residues from Grim, and 58 ordered water molecules at 1.9 Å resolution. For DIAP-BIR2 in complex with the Hid peptide, the final model contains residues 215–316 from DIAP I, the N-terminal 8 residues from Hid, and 36 water molecules at 2.7 Å resolution. The N-terminal 13–14 residues and the C-terminal 7–16 residues in DIAP1 have no electron density in the maps, and it is presumed that these regions are disordered in the crystals.

In vitro interaction assay. Interaction between the individual BIR domain of DIAP1 and the Hid/Grim peptides was examined by gel filtration chromatography. Approximately 0.5 mg of a recombinant BIR domain was incubated with excess Hid or Grim peptide for 20 minutes at room temperature. The mixture was fractionated by gel filtration chromatography (Superdex-200, Pharmacia). The protein-containing fractions were analyzed by reverse phase HPLC and mass spectroscopy for detection of the bound peptide.

Isothermal microcalorimetry titration. All proteins and peptides was prepared in 50 mM sodium phosphate buffer, pH 7.5. The Micro Calorimetry System (Microcal, Amherst, Mass.) was used to perform the ITC measurements for the interaction between DIAP1-BIR2 and various synthetic peptides. The titration data, collected at 23° C., were analyzed using the ORIGIN data analysis software (Microcal Software, Northampton, Mass.).

Results

Rationale and structure determination. Previous studies suggest that the BIR2 domain of DIAP1 is sufficient for interactions with the N-terminal sequences of the *Drosophila* proteins Hid, Grim, and Reaper. Therefore, the individual BIR1 (residues 1–145) and BIR2 (residues 201–325) domains were purified to homogeneity and these BIR domains were incubated with the N-terminal peptides of Hid and Grim. Gel filtration and mass spectroscopic analyses demonstrate that only the BIR2 domain forms a stable complex with the Hid or Grim peptide (data not shown). In contrast, no stable association was detected between the BIR1 domain and either peptide. Although the N-terminal 14 residues of Grim and Reaper share sequence homology, the conserved sequences among all three *Drosophila* proteins are restricted to the first 8 residues, suggesting a consensus binding element to DIAP1. Indeed, longer peptides from Grim exhibit the same binding affinity to DIAP1 as does a minimal 8-residue peptide (data not shown). Ten-residue peptides as derived from the N-terminal sequences of Grim and Hid were chosen for use. The N-terminal sequence of Reaper closely resembles that of Grim.

Binary complexes between Hid or Grim and DIAP1-BIR2 were purified by gel filtration and both complexes were crystallized. To assess possible conformational changes associated with peptide binding, the DIAP1-BIR2 domain by itself was also crystallized. The structure of the BIR2 domain by itself was determined by molecular replacement using atomic coordinates of XIAP-BIR3 as the initial search model (PDB code 1G73). The structures of peptide-bound BIR2 domains were solved by molecular replacement using the atomic coordinates of the partially refined BIR2 domain. The final atomic models were refined at 2.7, 2.7, and 1.9 Å, respectively, for the BIR2 by itself and in complex with the Hid and Grim peptides. All three structures exhibit excellent stereochemical parameters (Table 4).

TABLE 4

Data collection and statistics from the crystallographic analysis

| Data set (Spacegroup) | DIAP1-BIR2 (I4) | BIR2-Grim (P6$_5$22) | BIR2-Hid (P6$_5$22) |
| --- | --- | --- | --- |
| Resolution (Å) | 99.0–2.7 | 99.0–1.9 | 99.0–2.7 |
| Total observations | 36,725 | 244,305 | 87,781 |
| Unique observations | 7,220 | 12,525 | 4,535 |
| Data coverage (outer shell) | 95.1% (95.5%) | 98.8% (97.3%) | 98.3% (98.4%) |
| R$_{sym}$ (outer shell) | 0.113 (0.437) | 0.052 (0.160) | 0.133 (0.381) |
| Refinement | | | |
| Resolution range (Å) | 20.0–2.7 | 20–1.9 | 20.0–2.7 |
| Number of reflections | 7,176 (all) | 11,697 (I > σ) | 4,519 (all) |
| R$_{working}$/R$_{free}$ | 24.6%/28.9% | 20.2%/24.3% | 21.7% (28.7%) |
| Number of atoms | 1588 | 1062 | 968 |
| Number of waters | 18 | 58 | 36 |
| R.m.s.d. bond length (Å) | 0.008 | 0.007 | 0.010 |
| R.m.s.d. bond angles (degree) | 1.334 | 1.253 | 1.434 |

R$_{sym}$ = $\Sigma_h\Sigma_i$ |I$_{h,i}$−I$_h$| /$\Sigma_h\Sigma_i$I$_{h,i}$, where I$_h$ is the mean intensity of the i obervations of symmetry related reflections of h. R = $\Sigma$ | F$_{obs}$−F$_{calc}$ | /$\Sigma$F$_{obs}$, where F$_{obs}$ = F$_P$, and F$_{calc}$ is the calculated protein structure factor from the atomic model (R$_{free}$ was calculated with 5% of the reflections).
R.m.s.d. in bond lengths and angles are the deviations from ideal values, and the r.m.s.d. deviation in B factors is calculated between bonded atoms.

Figure 5:
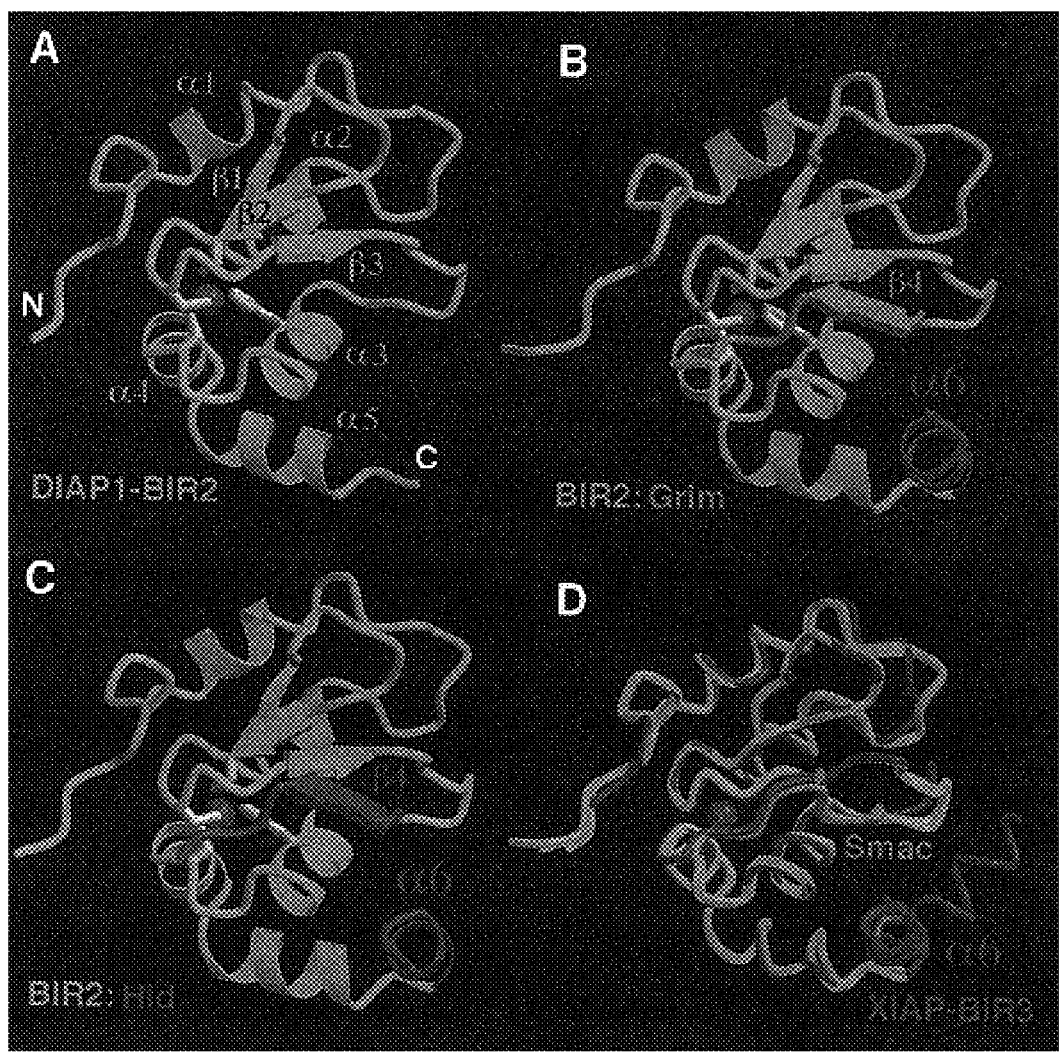
FIG. 5. Schematic diagram showing overall structure of the DIAP1-BIR2 domain by itself (FIG. 5a) and in complex with the Grim (FIG. 5b) or Hid (FIG. 5c) peptide. The DIAP1-BIR2 domain is shown in cyan and the bound Grim and Hid peptides are highlighted in orange and pink, respectively. The zinc atom in the BIR domain is colored red while its coordinating residues are shown in yellow. Some of the secondary structural elements are labeled.
Figure 6:
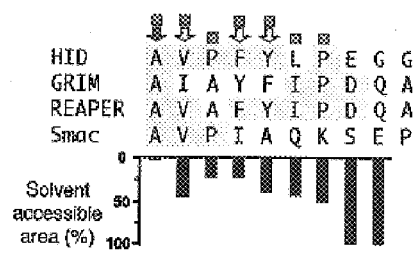
FIG. 6. Schematic diagram showing sequence alignment of the N-terminal peptides from Hid (SEQ ID NO:15), Grim (SEQ ID NO:16), Reaper (SEQ ID NO:17) and Smac (SEQ ID NO:18) (FIG. 6a) and of the BIR domains from DIAP1-BIR2 (SEQ ID NO:30), DIAP-BIR1 (SEQ ID NO:19), XIAP-BIR3 (SEQ ID NO:20), XIAP-BIR2 (SEQ ID NO:21), XIAP-BIR1 (SEQ ID NO:22), and survivin (SEQ ID NO:23) (FIG. 6b). The zinc-chelating residues are shown in red whereas the conserved amino acids are highlighted in yellow. Red and yellow arrows identify those residues that make intermolecular hydrogen bonds using their side chain and main chain atoms, respectively. The solvent accessibility for the peptides (FIG. 10a) and the secondary structural elements for the DIAP1-BIR2 domain (FIG. 10b) are indicated below the sequence alignment.
Figure 6:
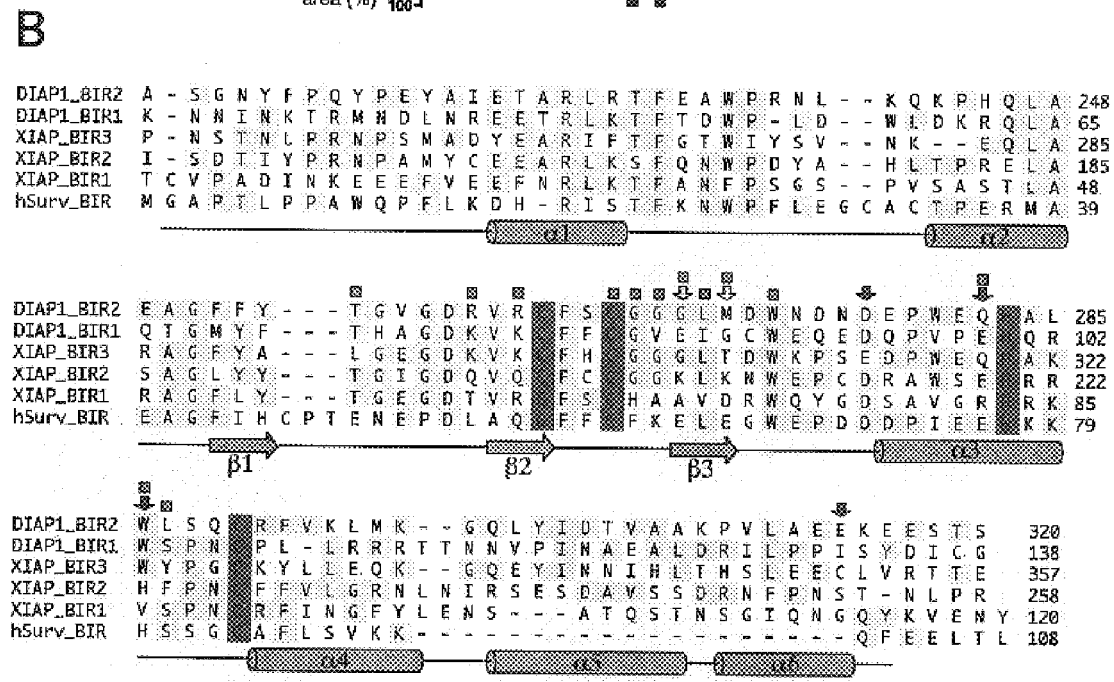

Structure of DIAP1-BIR2. The final atomic model of DIAP1-BIR2 by itself contains residues 215–309, comprising five α-helices, a three-stranded β-sheet, and a zinc atom chelated by three Cys and one His residues (Cys263, Cys266, His283, and Cys290) (FIGS. 5 & 6). The structure is similar to those of other BIR domains in XIAP and survivin, with root-mean-square-deviation (RMSD) of less than 2 Å for all aligned Cα atoms.

An 8-residue peptide from Hid or Grim binds a surface groove in an extended conformation, forming a fourth strand to the three-stranded β-sheet on DIAP1 (FIGS. 5b & 5c). Peptide binding appears to induce a major conformational switch in DIAP1, as shown by the formation of an additional α helix, α6 (FIGS. 5b & 5c). This helix (residues 310–316) is disordered in the apo form of BIR2, likely existing as a flexible loop in solution. Upon binding by the Hid or Grim peptide, this region adopts a helical conformation (FIG. 5) and stabilizes peptide-binding through hydrogen bonds. Residues on this helix (α6) closely pack against surrounding residues on helix α3 through networks of hydrophobic interactions.

Except for the newly formed helix α6, both the backbone and the side chains of the residues that comprise the peptide-binding groove remain identical before and after recognition by the Hid or Grim peptide. In this respect, the binding groove is fairly rigid, and the recognition can be described as a precise lock-and-key docking although helix α6 also contributes significantly to peptide binding. The overall structure of DIAP1-BIR2 by itself can be superimposed to that bound by the Hid or Grim peptides with 0.54 and 0.53 Å RMSD, respectively, for 96 aligned Cα atoms (FIG. 5d). On the other hand, DIAP1-BIR2 domains bound by either Hid or Grim peptide are essentially identical, with 0.17 Å RMSD for all aligned Cα atoms. In addition, the peptide-bound DIAP1-BIR2 structure also closely resembles that of the mammalian DIAP1-BIR3 domain bound by the Smac peptide, with approximately 0.8 A RMSD for 95 aligned Cα atoms (FIG. 5d).

Figure 7:
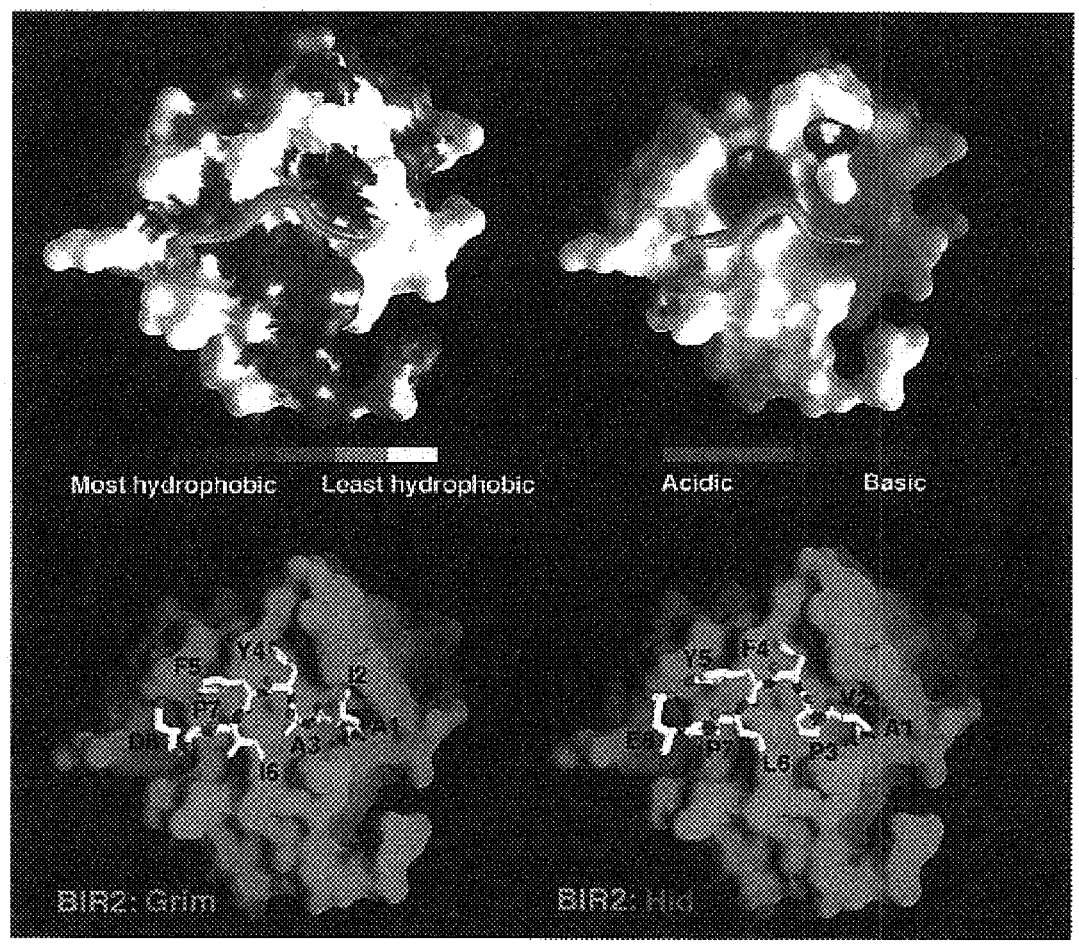
FIG. 7. Schematic diagram showing surface representation of the DIAP1-BIR2 domain bound to the Hid (red) and Grim (Green) peptides. The BIR2 surface is colored according to either the scale of hydrophobicity (top left panel) or electrostatic potential (top right panel).

Peptide-binding interface. Binding to the DIAP1-BIR2 domain results in the burial of 994 and 990 Å$^2$ surface area for the Hid and Grim peptides, respectively (FIG. 6). The recognition involves both hydrogen bond networks and extensive van der Waals contacts between seven hydrophobic residues on the peptides and surrounding DIAP1 residues. The eighth conserved residue on the peptides, Glu in Hid and Asp in Grim, exhibits well-defined electron density and points into the solvent phase, making no specific contact to DIAP1 (FIG. 7).

Figure 3:
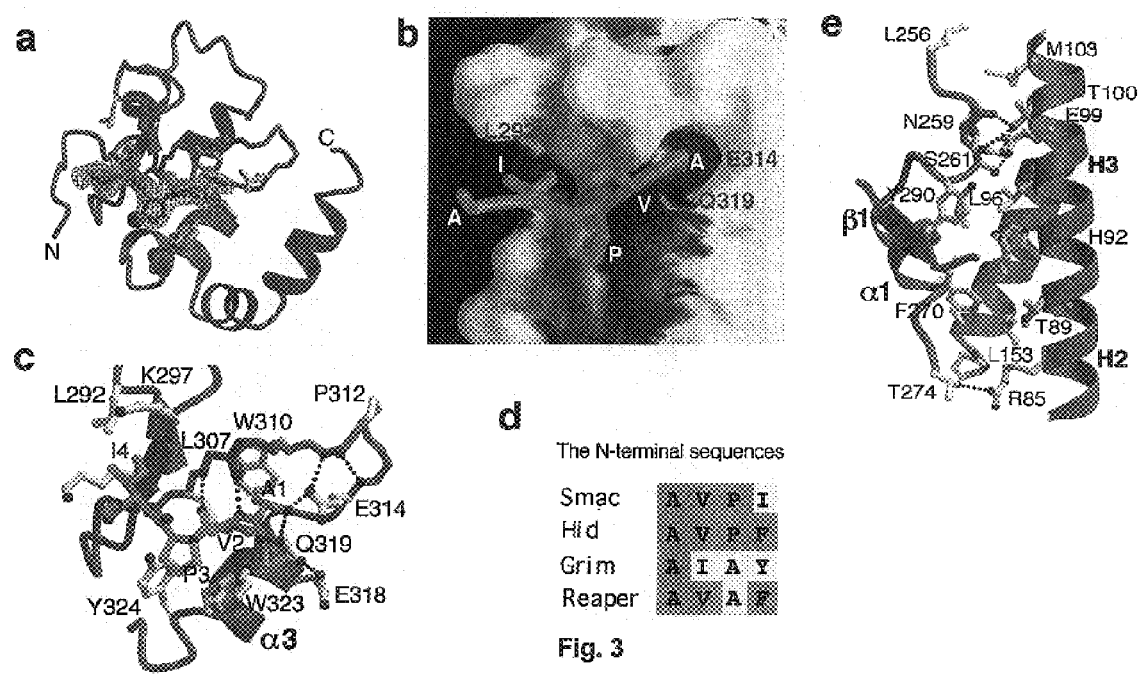
FIG. 3. Schematic representation of binding interface between Smac and XIAP-BIR3.
Figure 4:
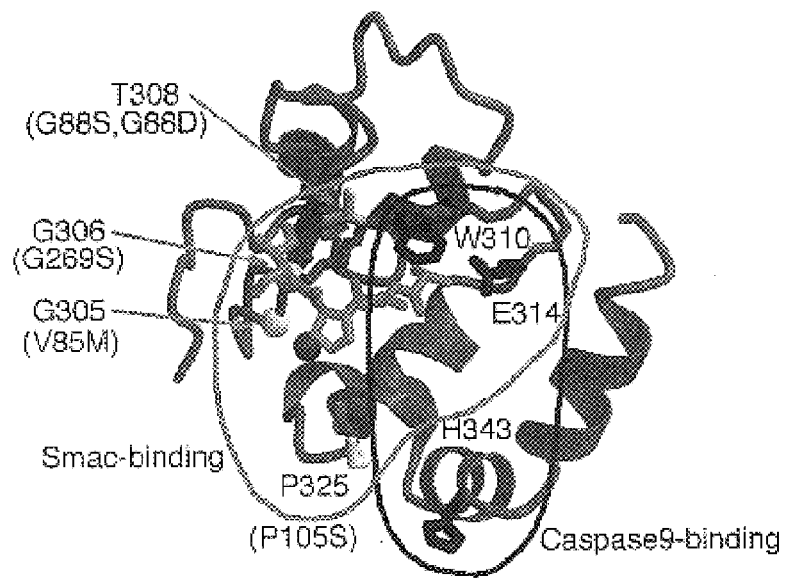
FIG. 4. Schematic diagram showing mechanism for the relief of XIAP inhibition of caspase-9 by Smac.
Figure 4:
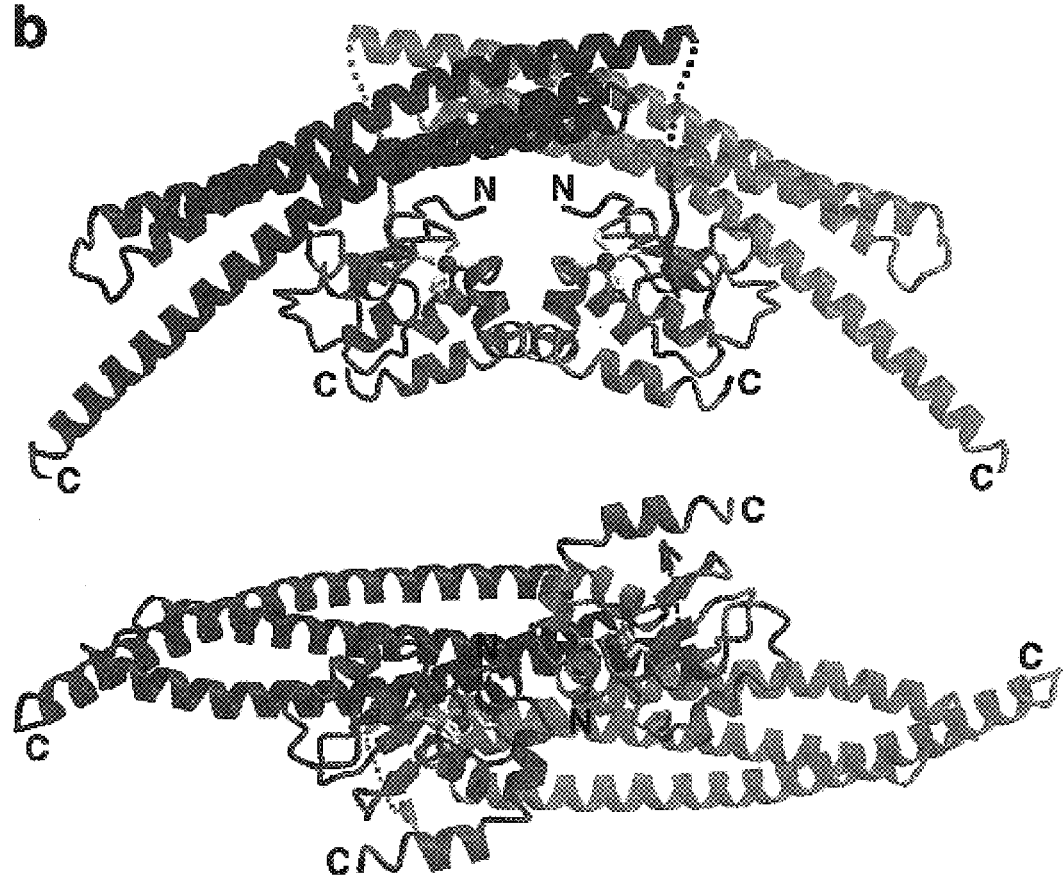

The peptide-binding surface on DIAP1 is enriched in hydrophobic residues (FIG. 3). These residues inter-digitate with the corresponding hydrophobic residues in the peptides through numerous contacts. The N-termini of these peptides are positioned in a highly negatively-charged environment (FIG. 7), in which two acidic residues (Asp277 and Glu314) in DIAP1 play an essential role in binding the Hid/Grim peptides.

For both Hid and Grim, a network of hydrogen bonds centered on Ala1 plays a central role in recognition specificity. In both cases, the amino group of Ala1 donates two hydrogen bonds to the surrounding residues Asp277 and Gln282 while the carbonyl group accepts two hydrogen bonds from the side chains of Trp286 and Glu314 (FIGS. 8a & 8c). These central interactions are buttressed by two intra-molecular contacts between the side chains of Glu314 and Gln282 and between the backbone groups of Asn274 and Asp277, respectively (FIGS. 8a & 8c). In addition, four inter-molecular hydrogen bonds among the backbone groups place the Hid and Grim peptides in an extended β strand conformation (FIGS. 8a & 8c).

Figure 8:
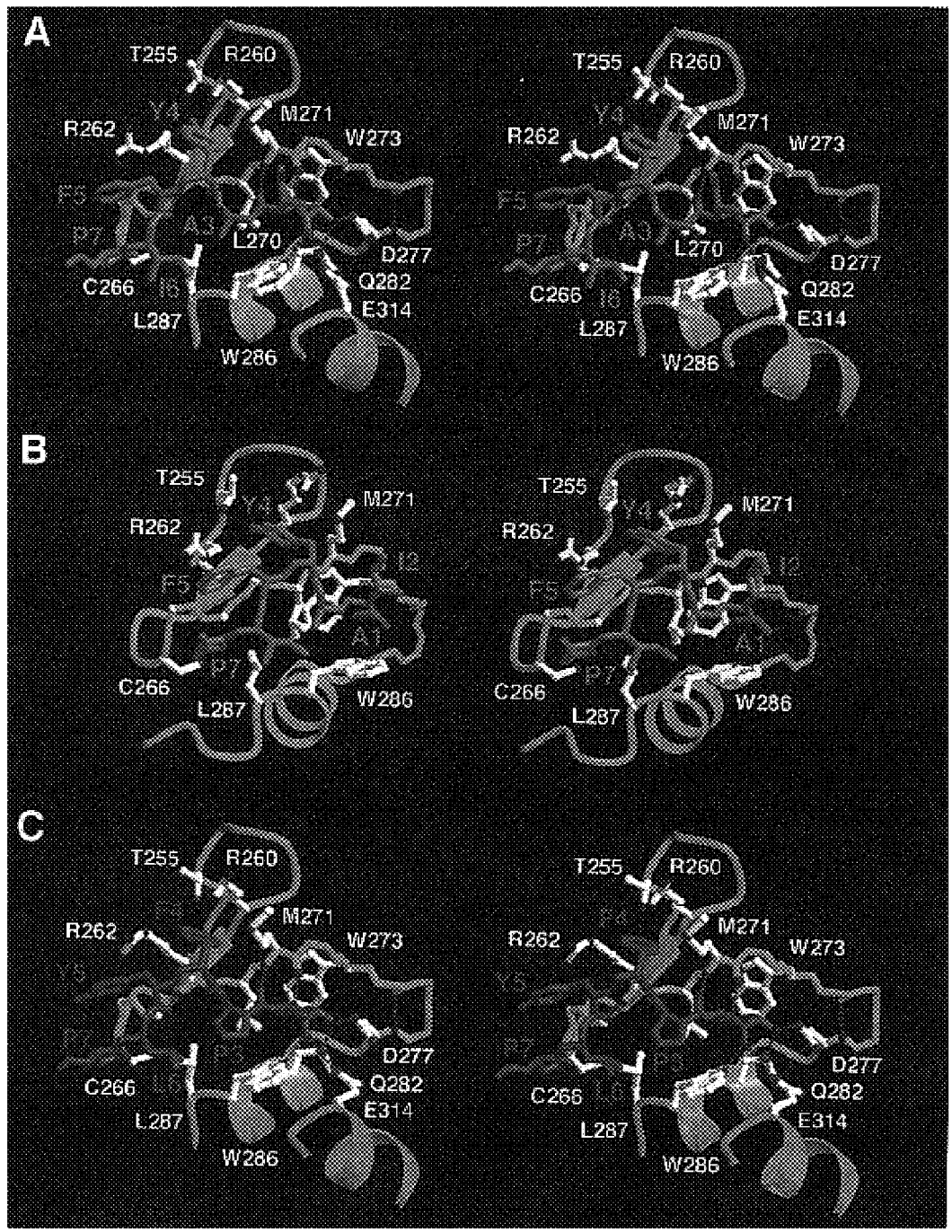
FIG. 8. Schematic diagram showing specific recognition of DIAP1-BIR2 by the Hid and Grim peptides.

Although hydrogen bonds appear to provide recognition specificity, van der Waals interactions play a dominant role in stabilizing the interactions between the Hid/Grim peptides and the DIAP1-BIR2 surface groove (FIG. 8). The methyl group of Ala1 fits tightly in a hydrophobic pocket formed by the side chains of Leu270 and Trp273 and the aliphatic portion of Gln282 (FIG. 8). The next six residues closely follow the hydrophobic surface groove on DIAP1 and make numerous van der Waals contacts (FIG. 8). Aside from the invariant Ala1 and Pro7, the intervening five residues are also conserved in Hid and Grim. These five residues mediate identical sets of interactions with the surrounding residues in DIAP1-BIR2 (FIG. 8).

Unique structural features. Studies on the recognition of XIAP-BIR3 by the Smac tetra-peptide suggested similar mode of interactions between the *Drosophila* proteins DIAP1 and Hid/Grim/Reaper (Example 1). This prediction was supported by reasonable sequence homology among the N-terminal four residues of the mammalian protein Smac and the *Drosophila* proteins Hid, Grim, and Reaper. Indeed, many of the critical interactions between the Hid/Grim peptides and DIP 1-BIR2 have been observed in the mammalian Smac-XIAP complex, including the anchoring role by Ala1 (FIG. 8). Despite this conserved theme, the *Drosophila* complexes exhibit two unique features.

In the mammalian complex, recognition is restricted to the N-terminal tetra-peptide of Smac; the fifth residue is not involved in binding the conserved surface groove on XIAP-BIR3. In the *Drosophila* complexes, however, three additional conserved residues make important contributions to DIAP1-binding through van der Waals contacts (FIGS. 6 & 8). These three residues stack against a hydrophobic surface groove comprising Cys266, Gly267, Gly268, Gly269, Trp286, and Leu287 on DIAP1, forming an extensive interface (FIG. 8b). The absence of side chains in the three consecutive Gly residues is likely a key determinant for the recognition of BIR2 by the Hid/Grim/Reaper peptides as this feature is not conserved in BIR1. There are also considerable intra-molecular packing interactions in the Hid/Grim peptides. For example, the fifth residue, Phe5 in Grim or Tyr5 in Hid, stacks against Pro7 while Ile6/Leu6 reaches out to contact Ala3/Pro3 (FIG. 8). The eighth residue, a conserved Glu/Asp in Hid/Grim/Reaper, does not interact directly with DIAP1 and points into the solvent phase. This unique mode of interaction agrees well with the observation that the N-terminal eight residues are conserved in Hid, Grim, and Reaper.

Figure 9:
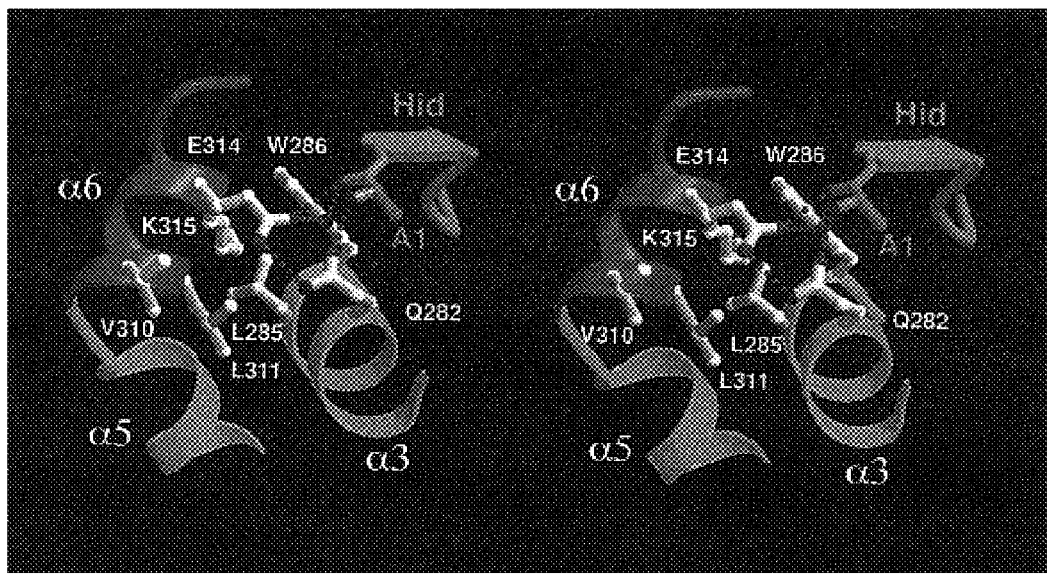
FIG. 9. Schematic diagram showing close-up view on the packing between helices α6, α3 and the bound peptide. Helix α6, induced upon peptide binding to DIAP1 and shown in red, makes important contacts to the bound Hid or Grim peptide (shown in orange). Glu314 on α6 hydrogen bonds to A1 of the Grim peptide, and Gln282 and Trp286 of DIAP1. There are numerous van der Waals interactions among the side chains of Val310/Leu311/Lys315 on α6 and Leu285/Trp286/Gln282 of helix FIG. 10. Graph and table showing quantification of the interactions between DIAP1-BIR2 and the Hid/Grim peptides.

In the peptide-bound structures of DIAP1-BIR2, there is an additional α helix (α6, residues 310–316). The constituent residues for this helix are completely disordered in the absence of peptide binding and become structured upon binding by the Hid/Grim peptides (FIG. 5). Supporting the large conformational switch, residues from this helix pack closely against helix α3 and contribute significantly to peptide binding (FIG. 9). At the periphery of the interface between helices α3 and α6, the carboxylate side chain of Glu314 on α6 donates one hydrogen bond to the carbonyl oxygen of Ala1 on the Hid/Grim peptides (FIG. 9). Buttressing this interaction, Glu314 makes two intra-molecular contacts to Trp286 and Gln282, respectively (FIG. 9). In the center, the packing interactions between this additional helix (α6) and the rest of the structure are predominantly hydrophobic in nature, involving four residues on α6 (Val310, Leu311, Glu314, and Lys315) and three residues on α3 (Gln282, Leu285, and Trp286) (FIG. 9).

Ligand diversity and DIAP1 recognition by Hid/Grim. In connection with the present invention's discovery of an important role by the N-terminal tetra-peptide of Smac, another highly conserved tetra-peptide motif has been identified by a computer search of the sequence of the mammalian protein procaspase-9, in accordance with the invention.

It has been determined that this motif is generated through proteolytic processing and subsequently involved in binding XIAP (Srinivasula et al., Nature 409, 112–116, 2001). Together with the N-terminal sequences of Hid/Grim/Reaper, these conserved tetra-peptides define a family of IAP-interacting motifs in both *Drosophila* and mammalian cells.

Although these N-terminal sequences are generally conserved, there are variations in the identities of the constituent amino acids in the *Drosophila* proteins Hid/Grim/Reaper and the mammalian proteins Smac and caspase-9. For example, the third residue can be either Ala (Grim/Reaper) or Pro (Hid, Smac, and caspase-9). Although Phe is preferred as the fourth residue (Hid/Reaper and caspase-9), Tyr (Grim) or Ile (Smac) can also be tolerated. The *Drosophila* proteins Hid/Grim/Reaper can induce apoptosis in mammalian cells, suggesting preservation of IAP-binding ability. Indeed, the N-terminal peptides of Hid and Grim interact with the mammalian protein XIAP (FIG. 10b). This observation raises an obvious question: what sequence elements in these peptides determine recognition specificity to the mammalian protein XIAP and the *Drosophila* protein DIAP1.

Figure 10:
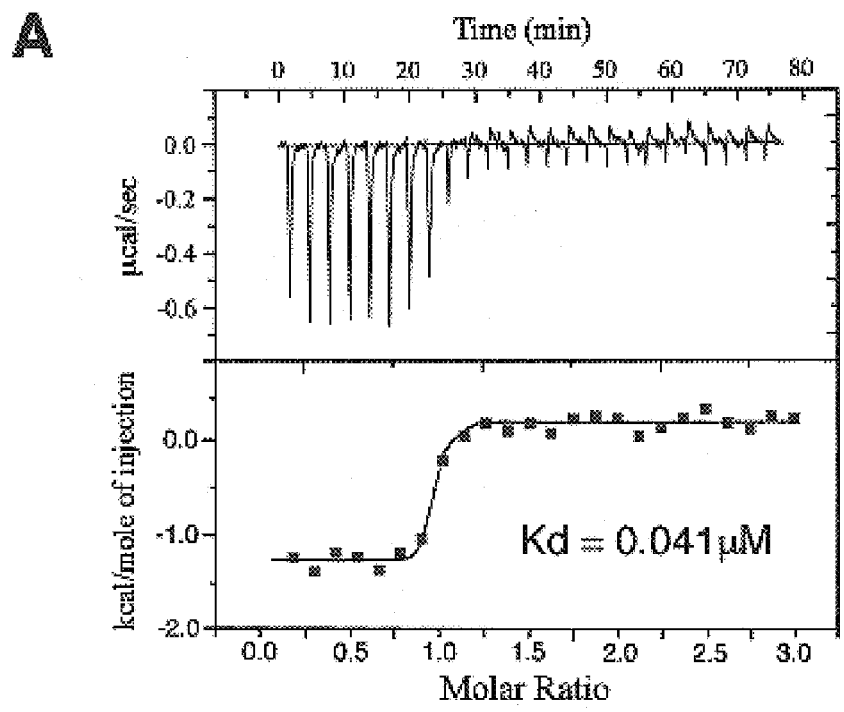

To address this issue, the binding affinities between the Hid/Grim peptides and the corresponding BIR domains in DIAP1 and XIAP were examined, using isothermal titration calorimetry (FIG. 10). Interestingly, the Hid peptide exhibits a 6-fold higher binding affinity to DIAP1-BIR2 than does Grim. This difference is likely due to the presence of Ala in the third residue position of Grim (Pro3 in Hid) as this is the only significant structural variation in binding (FIG. 8). A Pro residue in this position is likely to mediate more van der Waals interactions with Trp286 and Leu270 in DIAP1 (FIG. 8). Although both Grim and Hid peptides can bind to the mammalian XIAP-BIR3 domain, the binding affinity is different by nearly 100-fold (FIG. 10). Again, this large discrepancy is most likely due to variation in the third position, from Pro3 in Hid to Ala3 in Grim, because previous studies indicate that Pro3Ala mutation in Smac peptide reduced the binding affinity by approximately 50-fold.

EXAMPLE 3

Crystallography of a Functional DIAP1 Fragment Bound to Veto Peptide

Using methods similar to those set forth in the previous example, the DIAP1-BIR2 domain in complex with the N-terminal portion of the proapoptotic *Drosophila* protein Veto was crystallized and its structure analyzed. Crystallographic data and comparative data with respect to the Smac/XIAP interaction are set forth in Table 5 and Table 6 below.

TABLE 5

Data collection and statistics from the crystallographic analysis

| Data set | DIAP-BIR2/Veto peptide |
|---|---|
| Resolution (Å) | 99.0–2.1 |
| Total observations | 255,868 |
| Unique observations | 9,075 |
| Data coverage (outer shell) | 95.8% (94.1%) |
| $R_{sym}$ (outer shell) | 0.052 (0.145) |
| Refinement | |
| Resolution range (Å) | 20.0–2.1 |
| Number of reflections | 8881 |
| $R_{working}/R_{free}$ | 21.5%/28.4% |

TABLE 5-continued

Data collection and statistics from the crystallographic analysis

| Data set | DIAP-BIR2/Veto peptide |
|---|---|
| Number of atoms | 1002 |
| Number of waters | 116 |
| R.m.s.d. bond length (Å) | 0.009 |
| R.m.s.d. bond angles (degree) | 1.472 |

$R_{sym} = \Sigma_h \Sigma_i |I_{h,i} - I_h| / \Sigma_h \Sigma_i I_{h,i}$, where $I_h$ is the mean intensity of the i observations of symmetry related reflections of h. $R = \Sigma |F_{obs} - F_{calc}| / \Sigma F_{obs}$, where $F_{obs} = F_p$, and $F_{calc}$ is the calculated protein structure factor from the atomic model ($R_{free}$ was calculated with 5% of the reflections). R.m.s.d. in bond lengths and angles are the deviations from ideal values.

TABLE 6

Conserved interactions between DIAP1-Veto and XIAP-Smac.

Inter-molecular hydrogen bonds:

| DIAP1-Veto: | | Corresponding interactions in XIAP-Smac: | |
|---|---|---|---|
| Veto | DIAP1 | Smac | XIAP |
| 1 N | 277 OD2 | 1 N | 314 OE2 |
| 1 N | 282 OE1 | 1 N | 319 OE1 |
| 1 O | 286 NE1 | 1 O | 323 NE1 |
| 1 O | 282 NE1 | 1 O | 319 OE1 |
| 2 N | 271 O | 2 N | 308 O |
| 2 O | 271 N | 2 O | 308 N |
| 4 N | 269 O | 4 N | 306 O |

Intra-molecular hydrogen bonds at the peptide binding pocket:

| DIAP1-DIAP1: | | Corresponding interactions: | |
|---|---|---|---|
| DIAP1 | DIAP1 | XIAP | XIAP |
| 277 N | 274 O | 314 N | 311 O |
| 277 OD2 | 274 N | 314 OE1 | 311 N |
| 282 NE2 | 314 OE2 | 319 NE2 | 318 OE1 |
| 282 NE2 | 314 OE1 | | |

Inter-molecular van der Waals contacts:

Corresponding interactions:

| Veto (Smac) | DIAP1 (XIAP) |
|---|---|
| Ala 1 (Ala 1) | Leu 270 (Leu 307) |
| | Trp 273 (Trp 310) |
| Ile 2 (Val 2) | Trp 286 (Trp 323) |
| Pro 3 (Pro 3) | Leu 270 (Leu 307) |
| | Trp 286 (Trp 323) |
| Phe 4 (Ile 4) | Met 271 (Leu 292) |
| | Gly 269 (Gly 306) |
| | Arg 260 (Lys 297) |
| | Arg 262 (Arg 299) |

EXAMPLE 4

Functional Analysis of IAP-Binding Tetrapeptides

Figure 11:
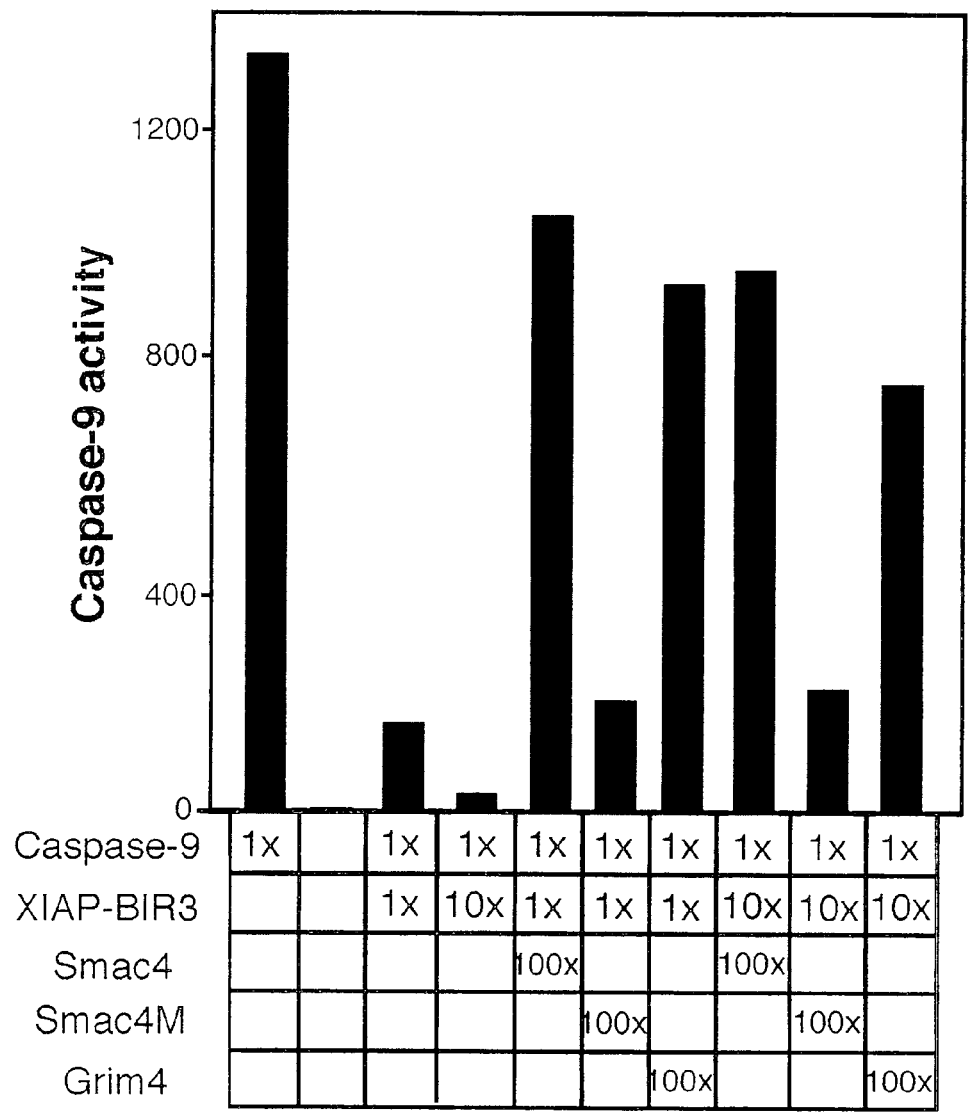
FIG. 11. Histogram and table showing effect of tetra-peptides derived from the human protein Smac (AVPI, SEQ ID NO:1; MVPI, SEQ ID NO:24) and from the *Drosophila* protein Grim (AIAY, SEQ ID NO:3) on relief of the inhibition of caspase-9 by the BIR3 domain of XIAP. The caspase-9 substrate Ac-LEHD-AFC was used at a concentration of 30 $\mu$M. The excitation and emission wavelengths are 390 and 505 nm, respectively. The concentrations of caspase-9 (1×), XIAP-BIR3 (1×), and peptides are 20 nM, 20 nM, and 2 $\mu$M, respectively.

FIG. 11 shows, in a direct assay for caspase-9 activity, that tetrapeptides derived from the human protein Smac and the *Drosophila* protein Grim relieve the inhibition of caspase-9 by the BIR3 domain of XIAP. In contrast, the mutant peptide Smac4M was unable to relieve the inhibition of XIAP-BIR3.

Figure 12:
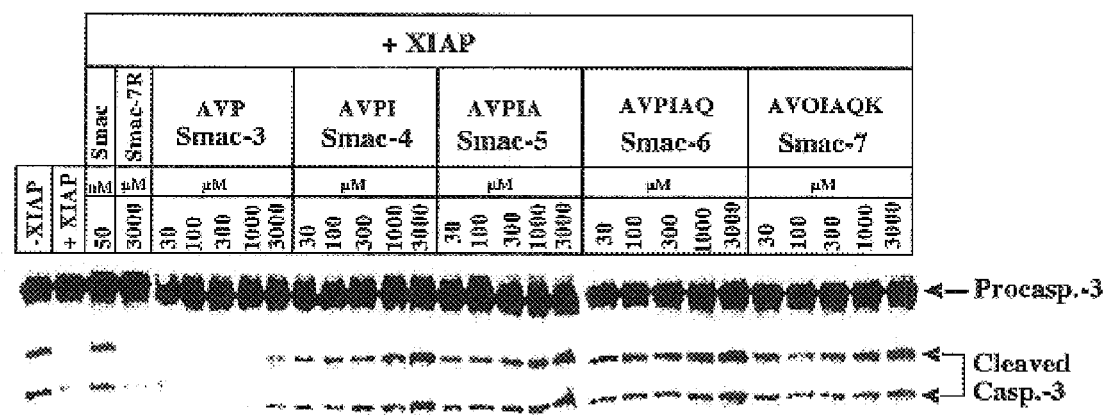
FIG. 12. Annotated autoradiogram showing effect of Smac $NH_2$-terminal peptides on relief of inhibition of XIAP on caspase-9 activation. 30 to 3000 $\mu$M of $NH_2$-terminal peptides of mature Smac with 3 to 7 amino acids in length were assayed for caspase activation in a reconstituted system consisting of recombinant Apaf-1(38 nM), procaspase-9 (12 nM), XIAP (40 nM), purified cytochrome c (500 nM), and in vitro translated $^{35}$S-labeled procaspase-3. The procaspase-3 cleavage activity was measured by phosphorimaging. Mature Smac and inactive peptide Smac-7R are included as controls.

FIG. 12 shows the results of an indirect caspase-9 activity assay in which caspase-3 cleavage is monitored as an indicator for caspase-9 activity. Again, Smac amino-terminal peptides relieved the inhibition of XIAP on enzymatic activity of caspase-9.

Figure 13:
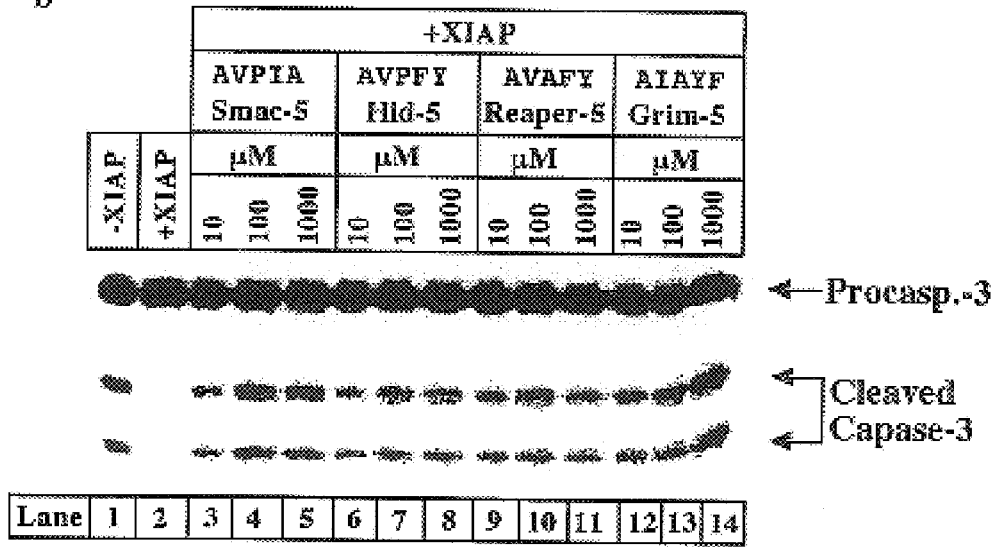
FIG. 13. Effect of Drosophila pentapeptides, Hid-5, Reaper-5, and Grim-5 on XIAP inhibition on caspase-3 activation.

FIG. 13 shows, in the indirect caspase-9 activity assay, that *Drosophila* pentapeptides, Hid-5, Reaper-5 and Grim-5 counteract XIAP-mediated inhibition of procaspase-3 activation.

Figure 14:
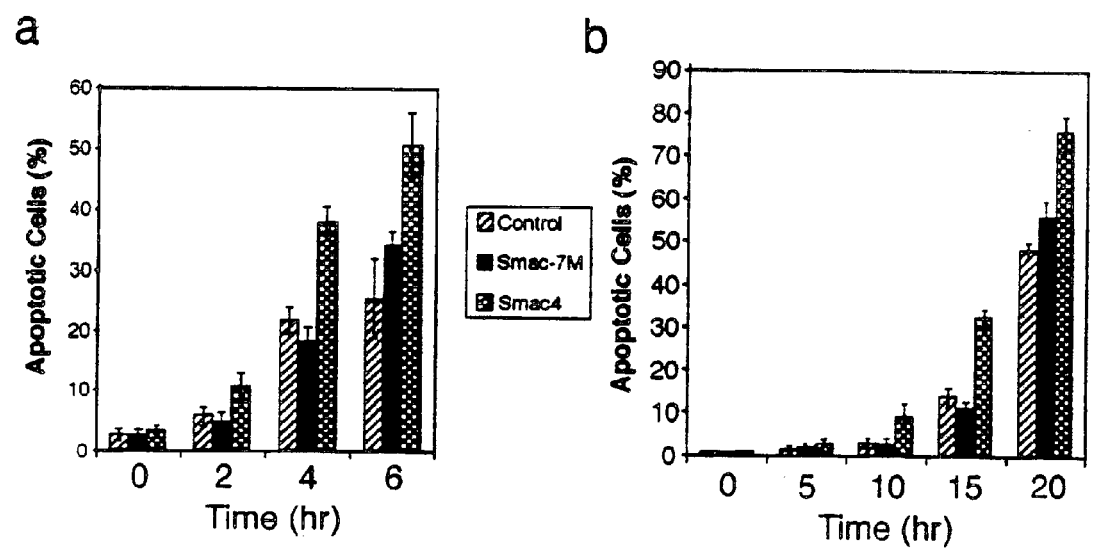
FIG. 14. Effect of Smac tetrapeptide on apoptosis in HeLa cells induced by UV and Etoposide treatment. HeLa cells were untreated (Control), or treated with Samc peptides for 12 hr followed by UV radiation (FIG. 14a) or Etoposide treatment (FIG. 14b). At each time point, the number of apoptotic cells manifesting condensed nuclei as stained by DNA dye Hoechst 33342 were counted and the percentage of cells that were apoptotic was plotted. Smac-7M peptide is used as a peptide control.

FIG. 14 shows that the Smac tetrapeptide potentiates apoptosis in HeLa cells induced by UV and Etoposide treatment.

The present invention is not limited to the embodiments described and exemplified above, but is capable of variation and modification within the scope of the appended claims.

What is claimed is:

1. A composition comprised of a peptidomimetic of a tetrapeptide having sequence X1-X2-X3-X4 wherein
   X1 is A,
   X2 is selected from the group consisting of V, T, and I,
   X3 is selected from the group consisting of P and A,
   X4 is selected from the group consisting of F, Y, I and V, and
   wherein said peptidomimetic is capable of binding a BIR-3 domain of an Inhibitor of Apoptosis Protein (IAP), wherein at least one of the amino acids is replaced with a modified amino acid, or at least one of the peptide bonds is replaced with a peptide bond substitute, and wherein the binding within a surface groove of the BIR-3 domain of the IAP is affected.

2. The composition of claim 1, said peptidomimetic relieves IAP-mediated inhibition of caspase activity.

3. The composition of claim 1, having an amino acid sequence substantially the same as a N-terminal sequence of cellular IAP-binding protein.

4. The composition of claim 3, wherein the cellular IAP-binding protein is a mammalian protein or a *drosophila* protein.

5. The composition of claim 1, wherein the tetrapeptide is selected from the group consisting of AVPI (SEQ ID NO. 1), AVAF (SEQ ID NO. 2), AIAY (SEQ ID NO. 3); AVPF (SEQ ID NO. 4); ATPF (SEQ ID NO. 5), AVPY, (SEQ ID NO. 6), and ATPV (SEQ ID NO. 7).

6. The composition of claim 5, which is AVPF (SEQ ID NO:4).

7. A method of stimulating apoptosis in a cell, comprising administering to the cell the composition of claim 1, in an amount sufficient to stimulate the apoptosis in the cell.

8. The method of claim 7, wherein the cell is a cultured cell.

9. The method of claim 7, wherein the cell is disposed within a living organism.

10. The method of claim 9, wherein the organism is a mammal.

11. The method of claim 9, wherein the mammal is a human.

12. A compound that binds a BIR-3 domain of an Inhibitor of Apoptosis Protein (IAP) and relieves IAP mediated inhibition of caspase activity, the compound having a formula R1-R2-R3-R4, wherein R1 is A or a mimetic of A;

R2 is V, T or I, or a mimetic of V, T or I;

R3 is P or A, or a mimetic of P or A;

R4 is F, Y, I or V, or a mimetic of F, Y, I or V; and wherein said peptidomimetic is capable of binding a BIR-3 domain of an Inhibitor of Apoptosis Protein (IAP), wherein at least one of the amino acids is replaced with a modified amino acid, or at least one of the peptide bonds is replaced with a peptide bond substitutes, and wherein the binding within a surface groove of the BIR-3 domain of the IAP is affected.

13. The compound of claim 12, which is a non-peptide or partial peptide mimetic of amino acid sequence selected from the group consisting of AVPI (SEQ ID NO:1), AVAF (SEQ ID NO:2); AIAY (SEQ ID NO:3), AVPF (SEQ ID NO:4), ATPF (SEQ ID NO:5), AVPY (SEQ ID NO:6) and ATPV (SEQ ID NO:7).

14. The compound of claim 13, which is a non-peptide or partial peptide mimetic of amino acid sequence AVPF (SEQ ID NO:4).

* * * * *